US 6,641,998 B2

(12) United States Patent
Sorge

(10) Patent No.: US 6,641,998 B2
(45) Date of Patent: Nov. 4, 2003

(54) METHODS AND KITS TO ENRICH FOR DESIRED NUCLEIC ACID SEQUENCES

(75) Inventor: Joseph A. Sorge, Wilson, WY (US)

(73) Assignee: Stratagene, La Jolla, CA (US)

( * ) Notice: Subject to any disclaimer, the term of this patent is extended or adjusted under 35 U.S.C. 154(b) by 0 days.

(21) Appl. No.: 09/288,971

(22) Filed: Apr. 9, 1999

(65) Prior Publication Data

US 2003/0036055 A1 Feb. 20, 2003

Related U.S. Application Data

(63) Continuation of application No. 08/948,458, filed on Oct. 10, 1997, now abandoned.

(51) Int. Cl.[7] .................. C12Q 1/68; C12P 19/34; C12N 15/64; C12N 1/20; C12N 5/02
(52) U.S. Cl. .................. 435/6; 435/91.2; 435/91.4; 435/91.52; 435/252.3; 435/325; 536/23.1
(58) Field of Search .................. 435/91.4, 91.2, 435/252.3, 325, 91.52; 536/23.1

(56) References Cited

U.S. PATENT DOCUMENTS

| | | | | |
|---|---|---|---|---|
| 5,354,656 A | * | 10/1994 | Sorge et al. ............ | 435/6 |
| 5,525,493 A | * | 6/1996 | Hornes et al. ........... | 435/91.2 |
| 5,624,826 A | * | 4/1997 | Kato et al. ............. | 435/91.4 |
| 5,770,443 A | * | 6/1998 | Kiefer et al. ........... | 435/325 |
| 6,238,923 B1 | * | 5/2001 | Passmore et al. ........ | 435/440 |

OTHER PUBLICATIONS

Prodromou et al, Protein Engineering, 1992, vol. 5(8), p. 827–829.*
Jayaraman et al., Nucleic Acid Research, 1989, vol. 17(11). p. 4403.*
Ivanov, Analytcal Biochemistry , 1990, vol. 89, p. 213–216.*
Dillon et al., Bio Techniques, 1990, vol. 9(3), p. 298–300.*
Shil et al., PCR Methods and Applications, 1993, vol. 3, p. 46–53.*
Stemmer et al. Gene, 1995, vol. 164(1), p. 49–53.*

* cited by examiner

Primary Examiner—Ethan Whisenant
Assistant Examiner—Joyce Tung
(74) Attorney, Agent, or Firm—Finnegan, Henderson, Farabow, Garrett & Dunner, LLP

(57) ABSTRACT

The invention provides a method and related kits and reagents for producing, purifying, isolating, or enriching desired nucleic acids from a library. The desired nucleic acids are produced from polymerase enzyme extension products, generated from specific primers or sets of primers, in a form that is immediately replicable in a host cell. The invention can be practiced in solution phase, thus eliminating the need for solid phase filter hybridizations, column hybridizations, or gel electrophoresis purification when enriching for or isolating a target sequence or vector from one or more libraries.

40 Claims, 2 Drawing Sheets

METHODS AND KITS TO ENRICH FOR DESIRED NUCLEIC ACID SEQUENCES

CROSS-REFERENCE TO RELATED APPLICATION

This application is a continuation of U.S. application Ser. No. 08/948,458, filed Oct. 10, 1997 now abandoned, which is incorporated by reference.

BACKGROUND OF THE INVENTION

1. Field of the Invention

The invention relates to techniques for manipulating nucleic acids linked to a vector. The methods described can be used, for example, in screening nucleic acid libraries. The methods can also be adapted to provide kits for screening nucleic acid libraries.

2. Introduction

The invention comprises methods and corresponding kits for enriching the presence of one or more desired nucleic acids from a collection of many nucleic acids. By employing the appropriate vectors and primers, the desired nucleic acids are produced in a replication-competent form that can be introduced into a host cell or organism. Thus, for example, the methods can be used with an appropriate bacteriophage library in order to directly produce, from the DNA of the library, replication-competent plasmids containing a desired nucleic acid. The resulting plasmids can immediately be transformed into appropriate hosts. The methods advance the ability of one skilled in the art to rapidly identify and isolate a desired nucleic acid in a vector. By directly employing the nucleic acids of a library rather than the hosts bearing those nucleic acids, the methods circumvent the steps of plating, growing, and transferring millions of clones in order to screen for a desired nucleic acid sequence. Unlike other methods directly employing the nucleic acids of a library, no physical separation or binding procedures are required. Thus, practice of this invention simplifies the screening of genomic, cDNA, or other nucleic acid libraries compared to currently used methods.

3. Description of Related Art

Nucleic acid libraries consist of a collection of different nucleic acids from a particular source, which possess differing nucleic acid sequences. Each of the nucleic acids, called "inserts," are operably linked to a vector with a particular nucleic acid sequence. The vector allows, inter alia, the nucleic acid inserts to be replicated in an appropriate host.

The nucleic acid molecules that make up a library are typically in circular or linear form. Plasmids are circular nucleic acid molecules that replicate in host organisms using an origin of replication and usually possess a gene that gives the host cell a selective advantage over other cells. Linear vectors, such as the bacteriophage lambda-derived vectors, may contain corresponding elements for replication and selection as well as elements encoding bacteriophage proteins necessary for propagation in bacteria.

Libraries of plasmid vectors typically contain the nucleic acid inserts at a defined location in the plasmid ("cloning site" or "multiple cloning site"). Linear vectors, such as lambda bacteriophage, will also typically contain the inserts at some fixed cloning site or multiple cloning site regions in the vector. The inserts are flanked by vector sequences of a particular design. For example, those skilled in the art have designed flanking regions to make "inserting" nucleic acids more convenient or easier. A number of vector designs have been developed and are well known in the art.

The libraries are generally constructed in order to facilitate the identification and isolation (cloning) of particular nucleic acid sequences, such as novel genes. Thus, it is often desirable to isolate one or more particular nucleic acids from a library for further study or use.

There are several ways to isolate a desired nucleic acid sequence from a library. Originally, in situ filter hybridization methods were used for this identification. (See, e.g., Sambrook, J., et al., Molecular Cloning, A Laboratory Manual, 2nd Ed., Cold Spring Harbor Laboratory Press, N.Y. (1989)) However, filter hybridization methods require intensive labor and a significant amount of materials. For example, the libraries are typically grown or plated on an appropriate surface as individual clones and then transferred to a filter membrane. Identification and separation of a desired clone, containing the desired nucleic acid sequence, requires physically locating a positively hybridizing bacterial colony or phage-producing plaque. Each library needs a certain minimum surface area so that an individual colony or plaque can be differentiated from others. As larger surface areas are needed, the number of filters for hybridization also increase. A hypothetical library of 1 million clones typically requires numerous 100 mm diameter filter membranes in order to screen one copy of the entire library. In addition, the filter hybridization screening methods require multiple rounds of colony plating or phage infection, filter preparation, and hybridization steps. Generally, one skilled in the art can screen up to one million clones effectively, but it may take weeks or months to yield the desired clone.

Other procedures have eliminated the time consuming aspects of filter hybridization. Instead, these procedures combine conventional hybridization with chromatographic or magnetic physical separation techniques. There are numerous examples. One method for isolating a particular plasmid from a mixture of plasmids relies upon hybridization of circular double-stranded plasmid DNA to a RecA protein-coated biotinylated probe. A resulting triple-stranded complex may then bind to an agarose-streptavidin column and be physically separated from other plasmids present. (Rigas, B. et al., P.N.A.S. 83: 9591 (1986)) Another modification employs biotinylated homopyrimidine oligonucleotide probes to form complexes that bind to streptavidin-coated magnetic beads. (Ito, T. et al., Nucleic Acids Res. 20: 3524 (1992); Ito, T. et al., P.N.A.S. 89: 495 (1992)) Takabatake et al. describe a variation of this technique that employs a biotinylated purine-rich oligonucleotide probe to bind the desired nucleic acid molecule. (Takabatake, T. et al., Nucleic Acid Res. 20: 5853–5854 (1992)) One drawback with using only homopyrimidine and purine-rich probes is the limitation in the possible nucleic acid sequences for which screening can be done.

Many other methods also employ a physical binding and separation step. Methods for screening libraries using biotinylated probes and magnetic beads are discussed in U.S. Pat. No. 5,500,356. Another method of screening for nucleic acid sequences is described by Kwok, P. Y. et al. This method, which employs PCR-based screening procedures, uses an ELISA-based oligonucleotide-ligation assay (OLA) to detect the PCR products containing the desired sequence. (Kwok, P. Y., et al., Genomics 13: 935–941 (1992)) OLA employs a "reporter probe" and a phosphorylated/biotinylated "anchor" probe. Streptavidin binding to the biotinylated probe can then separate the desired nucleic acids. (Landegren, U., et al., Science 241:1077–1080 (1988)) Biotin-streptavidin systems also rely on physical binding efficiency and may have the added problems of incomplete biotinylation of the probes used, which results in non-biotinylated probes hybridizing and failing to be separated by the physical technique used, as well as limited accessibility of the biotin on the probe.

In library screening methods, the ability to increase the abundance of a particular nucleic acid relative to all other nucleic acids present in a library is limited by the effectiveness of the physical separation technique used. A general drawback to all of these techniques is their reliance on physical binding and separation steps, which are inefficient and complicated.

A method that employs PCR amplification from cDNA libraries for obtaining additional nucleotide sequence of a desired gene when only a partial sequence is known is discussed in PCT 213 publication WO 96/38591. In that method, a PCR reaction extends primers directed to the cDNA insert sequences on circular plasmids. The extended, double-stranded DNAs from the PCR can be purified and re-ligated to generate the same plasmid with the same insert. Thus, plasmids containing target inserts may be amplified from a cDNA library. However, this method requires circular plasmids. Furthermore, the method also involves time-consuming steps after the PCR amplification. The publication discusses how the PCR reaction products, the extended, double-stranded DNAs, are purified by gel electrophoresis and then re-ligated to generate the plasmid with cDNA insert.

Another method that employs PCR in generating site-specific mutants is discussed in Jones et al. (Methods: A Companion to Methods in Enzymology, vol. 2, no. 1, February, 1991, pp. 2–10; see also U.S. Pat. No. 5,286,632). This method also employs circular plasmids as a starting material. Two PCR primers are used to extend a DNA from a circular plasmid. The 5' end of the primers used contains a region that is complementary to a region of two separate primers, which are used to extend a second DNA from a separate circular plasmid. These 5' ends remain single-stranded to provide cohesive ends to the PCR products. The two extended PCR products can be combined in vitro or in vivo to form a circular plasmid. The mutations can be introduced by using nucleotide changes within the primer sequence or by incorporating a sequence from the complementary region of the primers into the final plasmid. Cloning methods have also been discussed that employ PCR for inserting target DNA into vectors (for example, U.S. Pat. No. 5,525,493, to Homes et al.). However, in the Homes et al. method, the vector sequences of the cloned DNA all derive from a single-stranded linear vector that is hybridized to the amplified target. Thus, the method of Homes et al. cannot produce a replication-competent vector directly from the DNA of a library since it requires additional vector sequences that are not amplified directly from the library.

In summary, current methods for isolating particular, desired nucleic acid molecules are restricted by time-consuming, material-intensive steps and/or by the limitations of physical separation techniques, and/or by the rarity of certain nucleic acid molecules in a library. Accordingly, a method that expedites the isolation of desired nucleic acids is highly desired in the art, particularly if the method simultaneously and conveniently purifies the desired nucleic acids.

SUMMARY OF THE INVENTION

The present invention provides a method and related kits for producing, purifying, isolating, or enriching desired nucleic acids from a library. The desired nucleic acids can be produced in a form that can be immediately replicated in a host cell. The invention is practiced in solution phase, thus eliminating the need for solid phase filter hybridizations, column hybridizations, or gel electrophoresis purification. In fact, no physical separation methods are required. Instead, the invention takes advantage of polymerization reactions, directed from appropriate primers, to enrich for desired nucleic acid sequences.

In a particular embodiment, the invention allows desired nucleic acid sequences to be enriched or isolated from a collection of nucleic acid sequences attached to replication-competent vector sequences, such as a library. For example, one embodiment employs two or more primer extension products, which are single-stranded replicas of regions of the insert/vector nucleic acid sequences, to make a complex that is capable of replication in host cells.

Specifically, in one aspect, the invention provides a method to enrich a desired, nucleic acid from a sample containing a mixture of nucleic acids. The method involves producing a vector having the desired nucleic acid insert from a sample comprising a plurality of different vectors. Initially, first and second extension products are generated from first and second primers, wherein the first and second primers anneal to complementary strands of the vector having the desired nucleic acid insert. One or both of the first or second primers contain a nucleic acid sequence found in the desired nucleic acid insert or its complement. The first and second extension products are capable of annealing to each other and together comprise a sequence for replication in a host and the desired nucleic acid insert. The step of generating first and second extension products may optionally be repeated. By combining and annealing the first and second extension products, a partially double-stranded, replication-competent vector is formed.

Typically, the mixture of nucleic acids is a nucleic acid library where certain nucleic acids, such as cDNA, have been inserted into at least one vector, preferably at least one linear vector. The vector may have substantially repeated sequences flanking the nucleic acid insert (especially where linear vectors are used). Many different types of vectors may be used, including plasmid, circular, linear, and bacteriophage lambda-derived vectors. One skilled in the art is familiar with numerous vectors that contain functional bacteriophage lambda sequences and thus are bacteriophage lambda-derived vectors. A particular advantage of the method is that the resulting replication-competent vectors can be directly transferred to and replicated by an appropriate host. More specifically, the method may initially involve denaturing the nucleic acid mixture so that primers can be annealed to particular sequences, such as the desired nucleic acid sequence or a sequence of the vector. The primers are extended to form extension products that can be annealed to generate a replication competent-vector comprising the nucleic acid insert. When there are two primers used, first and second extension products are generated. However, the method is not limited to the use of only two primers. The extension procedure may, optionally, be repeated until the desired nucleic acid sequence is sufficiently enriched with respect to other nucleic acid sequences in the mixture. In this way, generating the extension products alone can result in enrichment of the desired vector. In addition, one may optionally select against any nucleic acid sequences that have not been synthesized by an extension reaction. For example, by cleaving all library nucleic acid with an enzyme that will not cleave a newly synthesized extension product with incorporated modified nucleotides, only newly synthesized products will remain full-length. The procedures for using modified nucleotides in this way are described in copending U.S. application Ser. No. 08/442,993, filed Jan. 3, 1997, Ser. No. 08/779,355, filed Jan. 6, 1997, Ser. No. 08/592,938, filed Jan. 29, 1996, and Ser. No. 08/713,404, filed Sep. 13, 1996, specifically incorporated herein by reference. By cleaving all or substantially all but the extension products, the nucleic acids can be annealed to form a replication vector containing the desired nucleic acid. The other, remaining nucleic acids will not form replication competent-vectors. Thus, the enrichment of desired nucleic acids does not depend solely on the number of extension reactions performed.

In other embodiments, the extension products may be generated separately. The order in which the extension products are generated is not critical. Even when generated separately, the extension products may be made in the same reaction vessel.

The invention also includes embodiments where additional nucleic acid, generally having an additional vector sequence, are added to the annealing reaction of the nucleic acids of the first and second extension products. Together with the additional vector sequence, the first and second extension products comprise a sequence for replication in a host and comprise a desired nucleic acid insert. The first and second extension products are capable of annealing to the additional vector sequence, and the additional vector sequence is designed with that annealing in mind. After annealing, a partially double-stranded, replication competent-vector is formed.

The invention may also be incorporated into a kit, for example, a kit for performing one of the embodiments of the methods described. The kits of the invention may comprise specific primers and primer extension reaction or amplification reaction reagents.

Combining extension products, such as the first and second extension products, involves appropriate denaturing and annealing conditions and forms a partially double-stranded vector with the desired nucleic acid insert. This vector may be transformed directly into an appropriate host in order to purify or enrich for the desired nucleic acid.

The vector and primers used can be designed so that the host cell is capable of replicating the desired nucleic acid sequences and so that the transformed host cell containing the desired nucleic acid can be selected from other cells. Thus, the primers should be designed so that regions of the vector containing the replication and selectable marker elements of the vector, as well as the desired nucleic acid insert, are represented in the extension products. Many variations are possible. However, it is not crucial that any particular extension product contain any certain element or desired nucleic acid sequence. As long as the vector elements and the desired nucleic acid insert are represented in the combination of the first and second extension products, a replication competent-vector containing the desired nucleic acid insert will be generated. When the combination of the extension products results in a partially double-stranded vector, an optional repair step may be included to form a substantially double-stranded vector with desired nucleic acid.

Other aspects of the invention include PCR or other amplification reactions to extend the primers used. In a preferred embodiment, primer pairs may be used. For example, the primers can be selected and extended so that a first primer pair is capable of amplifying, in an amplification reaction such as PCR, an extension product comprising a region of the desired nucleic acid sequence (here, the insert) plus a portion of the vector sequence. A second primer pair is capable of amplifying, in an amplification reaction such as PCR, a second extension product, which may also comprise a region of the desired nucleotide sequence.

In this embodiment, the first extension product comprises a region of homology with the second extension product at its 3' and 5' termini. For example, the first and second extension products both comprise a sequence that is homologous to the sequence of the desired nucleic acid insert and a sequence homologous to a region of the vector. The homologous sequences in both of the extension products allows them to anneal to one another, thus forming a partially double-stranded vector. The primer pairs are selected so that the vector elements for replication in an appropriate host and a selectable marker are represented when the extension products are combined. Additional vector sequences may also be represented in the combination of first and second extension products. However, where the primer pairs anneal to the vector containing the desired nucleic acid insert is not crucial to the practice of the invention. Thus, numerous variations of primers or primer pairs can be made and used.

By combining the first and second extension products under appropriate denaturing and annealing conditions to permit regions of the first product to anneal to complementary regions of the second product, an annealed complex is formed comprising the desired nucleic acid sequence and vector replication and selection sequences. Optionally, one adds an enzyme having repair activity, such as a DNA polymerase, and nucleotide triphosphates under conditions that permit the enzyme to create double-stranded DNA. This repairs any single-stranded regions in the annealed complex. Preferably, this repair occurs under conditions where the enzyme having repair activity has little or substantially no strand displacement activity.

DETAILED DESCRIPTION AND SPECIFIC EMBODIMENTS OF THE INVENTION

Figure 1A:
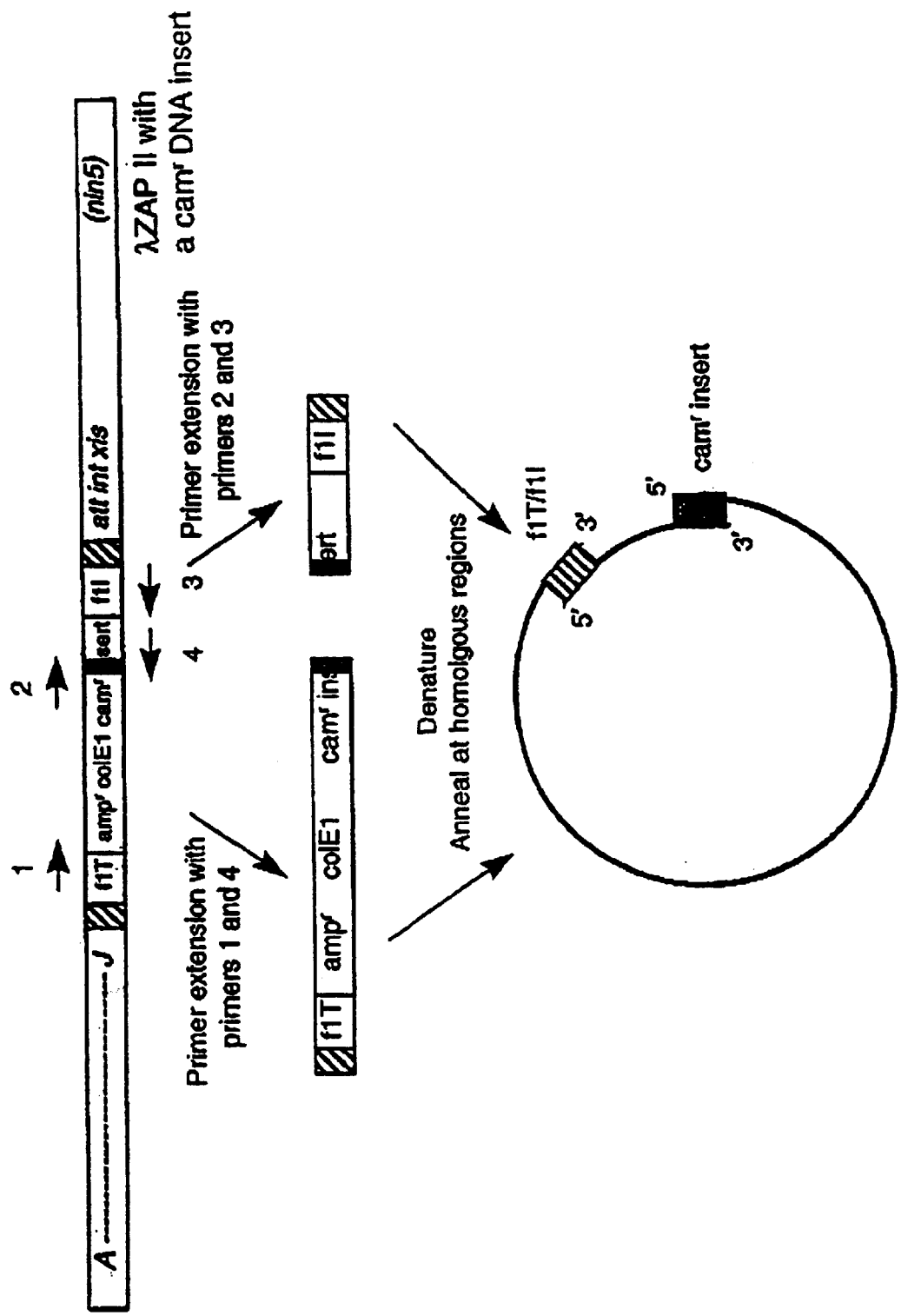
FIG. 1A depicts a representative Lambda ZAP® II vector with a nucleic acid insert encoding choramphenicol acetyltransferse (cam). The short arrows with numbers 1–4 above or below correspond to representative primers and their hybridizing regions on the vector. Extension of the primers produces first and second extension products shown directly below the Lambda ZAPS II vector map. These products contain complementary or homologous sequences at their termini. By denaturing and annealing the complementary sequences, the nucleic acid sequence of an entire plasmid with the desired insert sequence is formed. The gapped circle or partially single-stranded portion of the plasmid of this invention is represented at the bottom of the figure, and can be repaired to create a substantially double-stranded plasmid or used directly to transform a host cell.

The description below first provides options to consider in designing one of the various embodiments of the invention. For example, considerations for designing primers containing sequences annealing at particular sites in a vector are described for particular vectors. The primers need only anneal to a sequence of a vector during an extension reaction in order to function in the methods described and the kits for performing these methods. Generally, the primers are at least about ten nucleotides in length and may be much longer. One skilled in the art is familiar with methods to determine whether or not a specific primer can be used in a particular extension reaction. In addition, the annealing reaction, whereby a replication-competent vector is formed, may occur under a variety of conditions known in the art. Methods to determine the effectiveness of a particular annealing condition are also available to one skilled in the art. Optional repair steps are described as well as the step of adding additional plasmid sequences. The options given and described, which may be incorporated into the methods of the invention, should not be taken as a limitation of the invention. Following the description of options to consider, some of the embodiments are exemplified in the Examples.

In any embodiment of the invention, as discussed above, one may optionally select against nucleic acid sequences that have not been newly synthesized by an extension reaction, which may be an amplification reaction. For example, a newly synthesized extension product can have incorporated one or more modified nucleotides. An enzyme can be selected that is substantially incapable of cleaving at a site having one or more modified nucleotides. This enzyme will not cleave at any sites present on the newly synthesized extension product. However, it will cleave at sites without modified nucleotides. Adding the enzyme, thus, cleaves all nucleic acids in a mixture that are not newly synthesized and can effectively select against the undesired nucleic acids. Variations in enzymes, modified nucleotides, and strategies for employing this type of selection are described in copending U.S. application Ser. No. 08/442,993, filed Jan. 3, 1997, and Ser. No. 08/779,355, filed Jan. 6, 1997, specifically incorporated herein by reference. Accordingly, the invention is not limited to selection methods for enriching nucleic acids where only the newly synthesized extension products contain one or more modified nucleotides.

Also, as discussed above, in any embodiment of the invention the enriching for desired nucleic acids can be performed by transforming nucleic acids produced by the methods described into an appropriate host cell. The host cell containing the replication-competent vector produced by the methods of the invention, which also contains the desired nucleic acid, can be selected through the use of a selectable marker and corresponding selection agent. Combinations of selectable markers and selection agents are known in the art.

In this invention, all reactions are carried out in the solution phase. Screening in solution phase is very efficient and allows for the simultaneous screening of very large numbers of library members. Due to this high efficiency, one or more nucleic acid libraries can be combined and screened simultaneously with primers to isolate or enrich a desired nucleic acid(s) from one or more of the nucleic acid libraries. The primers selected for use need not be 100% homologous to the desired nucleic acid or the vector sequence. For example, a human-specific primer pair can be used to simultaneously screen nucleic acid libraries created from rat or mouse nucleic acid to identify rat or mouse homologs to the human sequence, or vice versa. Methods for determining the appropriate primer for a desired sequence, and the flexibility in the selected primer sequence allowed, are known in the art.

In addition, the primer or primers may be designed to introduce one or more point mutations, deletions, or insertions into the desired nucleic acid sequence. For example, the methods of the invention can be used to generate site-specific mutations. Procedures for designing embodiments of this invention where site-specific mutagenesis occurs can be found in copending U.S. application Ser. No. 08/220,374, filed Mar. 30, 1994, (entitled Cyclic Amplification Site-Specific Mutagenesis Methods and Compositions), specifically incorporated herein by reference.

Additionally, in any embodiment of the invention two or more sets of primers can be selected and used simultaneously to isolate or enrich two or more desired nucleic acids. Thus, the methods of the invention can be used to enrich more than one desired nucleic acid at the same time. This represents a significant advantage over current methods. Also contemplated is the simultaneous screening of two or more nucleic acid libraries.

Repair reactions used in the methods of the invention can repair a gapped or partially single-stranded nucleic acid molecule to form a substantially double-stranded molecule, as discussed herein. Also, the repair reaction should be carried out under non-strand-displacing conditions. Non-strand-displacing conditions can be determined as described in "Thermostable DNA Polymerases" in Methods of Enzymology, Vol. 48: 377–435, Academic Press, Inc. (1996), Kong, H., et al. J. Biol. Chem. 268: 1965–75 (1993), and the references therein, specifically incorporated herein by reference. Repair of the single-stranded nucleic acid molecule generates substantially double-stranded nucleic acids. The repair may increase the efficiency of transformation into host cells, thereby increasing the replication competence in the host cell used.

Any one of numerous known methods of primer extension can be used in the extension reactions contemplated in this invention. Functionally, generating an extension product involves enzymatically adding nucleotides or ribonucleotides to a primer that has annealed to a template. Extension reactions may use thermostable and thermolabile polymerases. The only requirement is that a primer annealed to the vector or desired nucleic acid and/or annealed to an extension product be a suitable substrate for the polymerase activity used. Accordingly, both the conventional primer extension reactions known in the art and the amplification reactions, such as PCR, can be used in the extension reaction to generate the extension products from the primer.

Specific examples of polymerase activities that may be selected for use include suitable thermolabile polymerases from mesophiles, available from many commercial sources, including *E. coli* pol 1, Klenow, T7 DNA polymerase, modified T7 DNA polymerase, T4 DNA polymerase, and the like. Suitable thermostable polymerases from thermophiles and hyperthermophiles are also available from commercial sources and include polymerases isolated from *Pyrococcus furiosus* (Pfu DNA polymerase; Stratagene, La Jolla, Calif.), *Thermus aquaticus* (Taq DNA polymerase; Stratagene, La Jolla, Calif.), *Thermococcus litoralis* (Vent DNA polymerase; New England Biolabs, Beverly, Mass.), Pyrococcus GB-D (Deep Vent, New England Biolabs), *Thermus thermophilus* HB8 (Tth; Perkin Elmer; Alamed, Calif.), *Bacillus stearmthermophilus, Thermus flavus* (Hot Tub DNA polymerase; Amersham; Arlington Heights, Ill.), *Pyrococcus woesei* (Pwo; Boehringer Mannheim, Indianapolis, Ind.), and the like. The polymerases may be purified from the native organism or be expressed and purified from a recombinant source.

The polymerases may have activities other than polymerase activity, such as 3'→5' exonuclease, 5'→3' exonuclease, endonuclease, and strand-displacement activities. For a review of thermostable DNA polymerases and their activities see "Thermostable DNA Polymerases" in Methods of Enzymology, Vol. 48: 377–435, Academic Press, Inc. (1996), specifically incorporated herein by reference.

Polymerases lacking strand-displacing activity are useful in practicing this invention. Polymerases having strand-displacing activity may be used under conditions which reduce or eliminate strand-displacing activity. Appropriate polymerase conditions, such as salt concentration, pH, and, in particular, temperature, are known in the art to affect strand-displacing activity. Also contemplated is the use of recombinant polymerases in which one or more mutations have been introduced into the nucleotide sequence, resulting in reduction or absence of strand-displacing activity.

The polymerases may be used separately or in combinations of two or more polymerases. Combinations of polymerases are available from commercial sources and include: GeneAmp® XL PCR Kit (Perkin Elmer; Alameda, Calif.), LA PCR Ki (Takara Shuzo Co., Ltd.; Shiga, Japan), Expand™ Long Template PCR System (Boehringer Mannheim; Indianapolis, Ind.), eLONGase™ Amplification System (Life Technologies; Gaithersburg, Md.), and TaqPlus DNA Polymerase Long (Stratagene; La Jolla, Calif.).

In addition, one skilled in the art is familiar with various nucleic acid extension reactions that can be modified for use with this invention. For example, one skilled in the art knows of the polymerase chain reaction, resulting in amplified DNA, and the RNA polymerase method, resulting in amplified RNA. (See, for example, Innis, M. A., et al. eds., *PCR Protocols*, Academic Press (1990); Innis, M. A., et al., eds., *PCR Strategies*, Academic Press (1995); U.S. Pat. Nos. 4,683,195; 4,683,202; 4,800,159; 4,965,188; 4,889,818; 5,075,216; 5,079,352; 5,104,792; 5,023,171; 5,091,310; and 5,066,58416) Various modifications and applications can also be employed in specific embodiments of this invention, as discussed in the references of the art. (For example, Erlich, H. A., ed., *PCR Technology*. Stockton Press (1989), Shah et al., J. of Medical Micro. 33(6): 1435–41 (1995); Stillman et al., PCR Methods and Applications 3(6): 320–31 (1994); Schochetman, G. and Sninsky, J. J., In: *AIDS Testing: A Comprehensive Guide*, Schochetman and George, eds., Springer-Verlag (1994)) Each of these references is specifically incorporated herein by reference.

The use of additives, which may enhance a desired result by changing the priming specificity of a primer and template or changing the polymerizing or strand-displacement activity and/or processivity of one or more of the polymerases used in a primer extension reaction and the like, is also contemplated. Suitable additives in the extension reactions are Perfect Match® DNA polymerase enhancer (Stratagene, La Jolla, Calif., U.S. Pat. No. 5,449,603), mutS (Wagner, R., et. al., Nucleic Acids Res. 23:3944–3948, 1995 and Takamatsu, S., et. al. Nucleic Acids Res. 24:640–647, 1996), betaine (Baskaran, N., et al., Genome Research 6:633638, 1996), dimethyl sulfoxide (DMSO, Hung, T., et al. Nucl. Acids Res. 18: 4953(1990)), formamide (Sarkar, G. et al. Nucl. Acids Res. 18: 7465 (1990)), tetramethylammonium chloride (TMAC; Chevet, E., et. al., Nucleic Acids Res. 23:3343–44, 1995), T-7 type single-stranded DNA binding protein (U.S. Pat. No. 5,534,407), gene 32 protein of phage T4 (Schwarz, K. et al. Nucl. Acids Res. 18: 1079 (1990)), PEF extracts or proteins (U.S. patent application Ser. No. 08/822,774, filed Mar. 21, 1997), and the like.

Methods for cloning a gene sequence once isolated or for manipulating nucleic acids are also well known in the art. In brief, these methods generally rely on the ability of a restriction endonuclease to cleave double-stranded DNA in a manner that produces termini whose structure (i.e. 3' overhang, 5' overhang, or blunt end) is defined. Any DNA molecule can, thus, be joined to a suitably cleaved vector molecule (i.e., another nucleic acid molecule, typically double-stranded DNA, having specialized sequences that permit replication in a suitable host cell) through the action of a DNA ligase. DNA molecules can also be joined to suitably cleaved vector molecules by ligation independent cloning. (See, for example, Aslanidis, C. et al., Nucl. Acids. Res. 18: 6069–6074 (1990)) The gene sequence may then be duplicated indefinitely by propagating the vector in a suitable host. (See, for example, Perbal, B. A., Practical Guide to Molecular Cloning, John Wiley & Sons, N.Y. (1984), especially pp. 208–217; Maniatis, T., et al., Molecular Cloning, A Laboratory Manual, Cold Spring Harbor Press, N.Y. (1982); Old, R. W., et al., Principles of Gene Manipulation, 2nd Ed., University of California Press, Los Angeles (1981); and Sambrook, J. et al, Molecular Cloning, A Laboratory Manual, 2nd Ed., Cold Spring Harbor Laboratory Press, N.Y. (1989), all herein specifically incorporated by reference.) As used herein, a vector derived from another vector, such as a vector derived from pCR-Script, is a vector that is made using the other vector and possesses substantially the same functional characteristics.

Representative sources of the nucleic acids that can be used with this invention specifically include: eukaryotic cells and organisms; prokaryotic cells and organisms; fungi; archaebacteria; plant cells and organisms; cells treated with viruses or phages or other infectious agents; cells containing heterologous nucleic acid; and cells created by fusion or related cell engineering techniques. Furthermore, one skilled in the art could readily adapt the teachings herein to any identified or synthesized nucleic acid source or sample incorporated into a nucleic acid library. Thus, one skilled in the art does not require an exhaustive list of potential nucleic acid sources.

Likewise, the type of vector used in a library is not crucial. For example, plasmid libraries, linear libraries, phagemid libraries, cosmid libraries, and other libraries can all be used, alone or even in combined pools. Specific examples include libraries made using a vector, or derived from a vector, of the following list: pCRScript™; pBluescript®; pBluescript®II; lambda phage vectors; lambda ZAP® and ZAPII; as well as any vector referenced in the Stratagene (La Jolla, Calif.) 1997–98 Catalog, which is specifically incorporated herein by reference. As long as the extension products of this invention can form a replication competent vector from the nucleic acid library selected, with or without additional vector sequences, one skilled in the art can utilize that particular type of library. A first vector is derived from a second vector if, for example, functional sequence elements are taken from the second vector and incorporated into the first vector. Alternatively, a first vector is derived from a second vector if the first vector contains a sequence, in the range of approximately 20 bp or more, identical to the second that is not also a required functional element of the vector. Random replication errors may create differences in vector sequences that would otherwise be identical and the presence of these errors does not negate a vector sequence being considered identical.

If desired, the complexity of the nucleic acid library can be reduced prior to performing the nucleic acid extension reaction. Typically, when nucleic acid libraries are produced, aliquots of the primary library are amplified separately and pooled to form an amplified library. The reduction in complexity can be accomplished by not pooling the amplified aliquots of the primary library. Another method to reduce the complexity is to reproduce aliquots of the amplified library by growth in a suitable host and to examine each aliquot separately.

In practicing this invention, one skilled in the art can use and is familiar with numerous appropriate conditions for denaturing and annealing nucleic acid samples, whatever the source, and how to determine optimum conditions for certain applications. The hybridization conditions used in PCR and in subtractive hybridization methods, known in the art and discussed in the above-noted references and elsewhere, exemplify this familiarity. For example, the conditions and degree of sequence similarity required for a primer to anneal to a vector sequence can be determined by considering known factors, as noted below. As long as the extension reactions can occur from the primer sequence under appropriate reaction conditions that can be determined through testing, the annealing is sufficient. That different primers may operate better under different conditions does not prevent the practice of this invention with a very broad number of possible primer sequences. In addition, the appropriate degree of sequence similarity and conditions for annealing the extension products of this invention operate to allow complementary or partially complementary sequences to hybridize into complexes that comprise certain vector sequences, as described, and the desired nucleic acid sequence. In appropriate circumstances, these conditions allow the sequences to form a circular plasmid. These conditions (time, temperature, denaturing strength of buffer, etc.) can also be readily determined by techniques known in the art, for example, by the $C_0t$ analysis and other related effects known in the art. (See, for example, Sambrook, J, et al., Molecular Cloning; Mathieu-Daudé, F., et al., Nucl. Acids Res. 24: 2080–2086 (1996); and Ausubel, F. M., et al. (1989) Current Protocols in Molecular Biology, Greene Publishing Assoc. and Wiley Interscience (including Supplement 34 (1996) and later supplements).) Numerous publications discuss appropriate annealing conditions to be used or be adapted for use with nucleic acid libraries and desired nucleic acids one may select.

In summary, the present invention offers advantages over other methods of screening for desired nucleic acids. For example, all reactions are carried out in solution phase, or can be, which allows very large numbers of library members to be screened in a relatively small volume. Physical separation methods, which can be cumbersome and depend on the quality of the solid phase components, need not be employed. Also, the use of PCR can vastly enhance the enrichment of the desired species. The end products are replication-competent; thus they can be propagated in a host cell and further amplified and studied.

The above descriptions and following examples provide specific embodiments of this invention. The inventors in no way limit the scope of this invention to these descriptions and specific examples. As noted, one skilled in the art is familiar with numerous techniques, which can be relied upon to modify or adapt the teachings of this disclosure. In addition, each of the embodiments discussed or referred to in this disclosure can be practiced by one of ordinary skill in the art in conjunction with the teachings herein. The discussions in the references cited, each specifically incorporated herein by reference, may be instructive.

Enrichment of a Desired Nucleic Acid in a Plasmid Library

The sequence selected for generating extension products containing a desired insert often contains the insert sequence, or an approximately 10 nucleotide or more part of it. In a plasmid library, primer extension products originating from a primer that anneals to a sequence within the insert will be extended 5' to 3' through the insert, an insert/vector junction, through the vector sequences, continue to the other insert/vector junction, and proceed along the other end of the insert until the original 5' end of the primer is encountered. This process can be used to generate a first primer extension product. If the polymerase that is synthesizing this first primer extension product has little or no strand displacement activity, the first primer extension product will terminate at the nucleotide immediately upstream of the nucleotide annealed to the 5' nucleotide of the primer.

A second primer extension product can be generated on a complementary strand of nucleic acid using a primer that anneals to a complementary strand of the insert sequence. This second primer extension product need not use the same template or plasmid molecule as used to generate the first primer extension product. However, the insert region of the second template should contain some sequence homologous to the first template, so that each primer extension product will contain some insert sequence that is complementary with the other primer extension product. If both insert/vector templates were completely complementary for both primer extension products (such as if both strands of a single plasmid were used to make both primer extension products or if identical copies of the plasmid are used), each primer extension product can be viewed as single-stranded circular molecule with a "nick" at a certain location in the circle (at the original 5' end of the respective primer). By dissociating the primer extension products from their templates, for example by heating, and subsequently allowing them to anneal to each other, the two primer extension products are capable of forming a double-stranded molecule with two nicks, one in each strand. If the 5' ends of the original primers used to make the primer extension products are at different positions in the annealed molecule, the two nicks will be offset from each other and the double-stranded molecule will be a circle with one nick in each strand located at different positions in the circle. Such circles are stable and can be transformed into host cells, where the nicks will be repaired by host kinases and ligases, yielding a replication-competent plasmid. Accordingly, by designing primers that generate first and second extension products with complementary insert sequences, such as primers that anneal to different regions of the insert nucleic acid, copies of a replication-competent plasmid containing the insert can be generated from a plasmid library.

Multiple rounds of extension reactions can be performed to further enrich for the desired replication-competent plasmid.

Repair of Gaps in Annealed Primer Extension Products

Primer extension products may not extend all the way around the plasmid "circle" to the 5' end of the primers. They may terminate prematurely, creating "gaps" in the circle subsequently formed by annealing the complementary extension products. Such gaps can be repaired either by a polymerase activity in vitro or a by a polymerase activity in vivo, in the host cell. However, the primer extension products should have sufficient complementarity of sequences to form at least a partially double-stranded, replication-competent molecule upon annealing of the extension products. For example one extension product can be replicated clockwise from a position corresponding to 350 degrees on a circle (the 5' end) to a position corresponding to 190 degrees on the circle. The second extension product can be replicated from the complementary strand beginning at a 5' position of 10 degrees on the circle and proceeding counterclockwise to a position of 170 degrees on the circle. Annealing these extension products together will form a gapped circle with double-stranded regions from 350 degrees to 10 degrees and from 170 degrees to 190 degrees. The remainder of the circle will be single-stranded. However, a polymerase activity is capable of extending the 3' ends (located at 170 degrees and 190 degrees) and extending them to their respective 5' ends. The extension to "repair" the partially single-stranded molecule to generate a substantially double-stranded molecule can be accomplished in vitro or in vivo. Accordingly, an optional in vitro repair step can be included in the methods of this invention.

Repair of Displaced Ends in Annealed Primer Extension Products

By displacing a primer from the template, with a strand displacement activity found in some polymerase compositions, a primer extension product extending beyond the 5' end of the primer results. The extension product, thus, contains more than one complete "circle" when considering the end of the primer as the beginning of the circle. The displaced ends could subsequently be trimmed by a single-stranded exonuclease, or by a DNA polymerase having 5' exonuclease activity, or by an enzyme such as Fen-1, which specifically recognizes the junctions caused by displaced strands. These modifications to the annealed complex could be carried out in vitro or would occur naturally in vivo with the appropriate host cell.

Enrichment of a Desired Nucleic Acid from a Linear Library: A Bacteriophage Library In preferred embodiments, a replication-competent plasmid can be produced from a library employing a linear vector, such as in lambda bacteriophage-derived vector. In one of these embodiments, the invention can be practiced provided there are directly repeated sequences in the vector regions flanking the insert, but not necessary immediately flanking the insert (referred to as the left and right vector "arms"). For example, a linear vector may contain a "cos site" as a repeated sequence at the ends of the vector. In this example, a primer extension product is extended from primers that anneal to the insert region to the terminus of the cos site, since the cos sequence is repeated at both ends of the linear molecules. An extension product whose 5' ends are in a complementary region of the insert would also be complementary at the cos ends. The extension products can be annealed to make a replication-competent complex, which in the case of lambda bacteriophage-derived vectors, would be a linear concatamer of several lambda genomes or a dimeric circular molecule. The single-stranded regions of such complexes could be repaired with a polymerase in vitro to increase the viability of such complexes in host cells.

The Lambda ZAP® and Lambda ZAP® II vectors are lambda vectors that were designed to contain plasmid replication, selection, and directly repeated sequences in the vector arms. (U.S. Pat. Nos. 5,128,256 and 5,286,636; Short, J. M., et al. Nucl. Acids Res. 16: 7583–7600 (1988).) Specifically, Lambda ZAP contains regions from the f1 phage origin of replication in both arms of the lambda vector such that portions of these f1 sequences are directly repeated. Between the insert and these left and right repeated f1 regions are plasmid replication and selection sequences (a col E1 origin of replication and a beta-lactamase gene, respectively). Insert-specific primers can be extended into the arms, replicating the f1 region in the extension products. A portion of the f1 region replicated in the right arm would be complementary to the f1 region replicated in the left arm, since the primer extension products would be using opposite strands of the lambda genome as templates. After annealing these primer extension products, the insert-specific complementary regions would anneal and the f1 complementary regions would anneal, forming a gapped circle.

If the primer extension products had proceeded beyond the f1 regions in the lambda arms, the 3' ends of the primer extension products would not be complementary to sequences in the gapped circle. Thus, the 3' ends would be displaced from and protrude from the gapped circle. The displaced sequences can be trimmed away with a single-stranded exonuclease and the like. However, 3' protrusions can be prevented from forming by first digesting the lambda DNA with a restriction endonuclease that cleaves the template DNA immediately distal to the both repeated regions but does not cleave the DNA between the two repeated regions. If the template DNA is first cleaved at such a restriction site, the primer extension products will terminate at the distal ends of the repeated sequences. Vectors can be designed having such restriction sites using methods well known to those skilled in the art. (See, e.g., Sambrook, J., et al., Molecular Cloning, A Laboratory Manual, 2nd Ed., Cold Spring Harbor Laboratory Press, N.Y. (1989)). It is important to recognize that the flanking repeated regions are not limited to f1 sequences or any other specific sequences. Additionally, the nucleotide sequence of the flanking, repeated regions need not have identical sequences but should be of sufficient homology to allow the two primer extension-products to anneal. Tests to analyze whether or not the extension products will anneal are well known in the art. The percent of sequence identity over a region required for a particular sequence to anneal to another may vary from as much as about 60% to about 90%, as recorded in the art. The flanking, repeated regions can be any directly repeated sequence. In other embodiments, directly repeated sequences are not required when the annealing reaction is supplemented or repaired with additional DNA that completes the plasmid "circle," as discussed below.

Cycled Primer Extension Reactions to Prepare Single-Stranded DNA

Regardless of whether the template is a circular or linear molecule, or whether the annealed complex contains nicks and/or gaps, the concentration of the desired annealed complex can be increased by repeating the primer extension steps prior to the annealing step. The primer extension steps can be repeated by denaturing the nucleic acids after each primer extension step, allowing additional primers to anneal to the original template molecules, and extending such primers with polymerase and substrate. Many cycles of such primer extension reactions can be repeated prior to the annealing step.

The cycled primer extension reactions here are not necessarily the same as the polymerase chain reaction since the primer extension products created in each cycle may not be suitable templates in subsequent primer extension reactions to form replication-competent complexes. One can employ primers that will not necessarily create replication-competent annealing complexes. For example, assume that for a circular template a first primer is designed to anneal at 350 degrees on the circle with a clockwise 5' to 3' polarity and the second primer is designed to anneal to the complementary strand at 10 degrees on the circle with a counterclockwise 5' to 3' polarity. The primer extension product created by the first primer could be used by the second primer as a template. However, such second primer extension product would only proceed counterclockwise from 10 degrees to 350 degrees before reaching the 5' end of the first primer. This second extension product would not contain sequences counterclockwise of 350 degrees. Thus it would not form a gapped circle with the first primer extension product and would not produce a replication-competent complex. However, if the primer that anneals at 10 degrees extends from the plasmid template, it is capable of being extended around the entire circle. Such an extension product would be a productive element of a replication-competent annealed complex. Therefore, one skilled in the art should take into account the direction of the extension reaction used as well as the complementarity of the primers in conjunction with the intended template for extension.

PCR and related reactions produce replicas of primer extension products. In these embodiments, such PCR products do not contribute meaningfully to the replication-competent annealed complex. Thus, these embodiments may use "linear amplification" of the original library template molecules to increase the concentration of desired annealed complexes, but "exponential amplification," such as that found in PCR, is not necessarily helpful to this specific embodiment.

Removal of Non-Extended Library Nucleic Acids

Regardless of whether linear amplification is used to increase the concentration of desired annealed complexes, it is desirable to decrease the concentration of the unwanted nucleic acids in a library prior to transformation of host cells. This can be achieved if the primer extension products are chemically different from the nucleic acids in the original library and a method is used to inactivate the replication competence of the non-extended, unwanted library nucleic acids. For example, DNA from *Escherichia coli* libraries is typically methylated at GATC sites resulting from the dam methylation system. However, primer extension products will not be methylated at GATC sites provided that the nucleotide triphosphates used in the primer extension reactions are not methyl modified. The restriction enzyme Dpn I will cleave DNA that is methylated at GATC sites but will not cleave DNA unmethylated at GATC sites. Thus, after the annealing step, the DNA can be treated with Dpn I to cleave the library DNA yet leave the primer extension product intact. This further enriches the mixture for replication-competent forms of the desired nucleotide sequence.

Alternatively, the primer extension reactions can be carried out in the presence of a modified nucleotide triphosphate such that the nucleic acids synthesized in vitro will be protected from cleavage by some enzyme or chemical that is inhibited by the modifications in the nucleotides. For example, 5-methyl-deoxycytosine triphosphate can be incorporated during the primer extension reactions. This will protect the newly synthesized DNA from cleavage by enzymes that do not recognize DNA with methylated cytosine residues. However the unwanted library DNA will be cleaved since the cytosines will not be methylated. Various modifications and adaptions to this optional step to remove unwanted library nucleic acids are possible.

Cycled Primer Extension Reactions to Prepare Double-Stranded DNA

Embodiments of the invention can also use the PCR process. Instead of making two complementary single-stranded primer extension products, the process makes two double-stranded PCR products that contain common sequences at both ends. For example, assume that a first PCR primer pair is designed to amplify a region of a circular plasmid clockwise from 350 degrees to 190 degrees, making a double-stranded molecule. A second PCR primer pair is then designed to amplify the region clockwise from 170 degrees to 10 degrees. The double-stranded PCR products will contain common sequences between 170 to 190 degrees and between 350 degrees and 10 degrees on both molecules.

If both PCR products are mixed, denatured, and then annealed, replication-competent complexes will form in addition to the simple reannealing of the original strands. Such replication-competent complexes will be gapped circles with double-stranded regions between 350 degrees and 10 degrees and between 170 degrees and 190 degrees. A non-strand displacing DNA polymerase is then used to extend the 3' ends of the annealed molecules to create fully double-stranded circles with staggered nicks. Such nicked circles are replication-competent and have a high transformation efficiency.

The PCR method can be used to create replication-competent complexes from linear DNA as well. For example with Lambda ZAP, two sets of PCR primers can be designed. One set amplifies the region from the "left" f1 repeat (f1 terminator) to some location in the desired nucleic acid sequence (see FIG. 1). The second set amplifies the region starting from some location "left" of the termination site of the first PCR product in the desired nucleic acid sequence to the "right" f1 repeat (f1 initiator). Thus, the two PCR products will have common terminal sequences from the desired nucleic acid sequence and from the f1 repeats. When such products are mixed, denatured, and reannealed, replication-competent complexes will form, which can optionally be treated with a DNA polymerase to create fully double-stranded gapped circles.

Since the PCR products are double-stranded, two replication-competent complexes can form after mixing and annealing the two products. One is comprised of 'strand A' from PCR product 1 and "strand B" from PCR product 2; the other is from "strand B" from PCR product 1 and "strand A" from PCR product 2. Both should be equally replication-competent and lead to the same final product in vivo.

PCR allows for substantial enrichment of the desired species over the unwanted species. Since each PCR product is synthesized with one vector-specific primer and one insert-specific primer, the resulting PCR product will be greatly enriched for the desired nucleic acid. Enrichment can be enhanced even further by using a nested PCR approach, as known in the art. A nested insert-specific primer can be used in a second round of PCR to increase the specificity of the PCR product. Such enrichment diminishes the need to cleave the library DNA prior to transformation.

Formation of Replication-Competent Vectors/Complexes by Adding Additional Nucleic Acid In general, the annealing reaction can be supplemented with additional nucleic acids that can facilitate the formation of a replication-competent vector or complex. For example, assume that for an insert cloned in a lambda vector, two PCR products are created such that the products extend from the desired nucleic acid sequence distally to just beyond the insert/vector junctions. (These products need not be created by PCR; simple primer extension reactions would create equally useful products.) The products would not be able to form a replication-competent complex by themselves since they would be lacking sequences needed for replication in the host cell. The replication sequences could be added to the annealing reaction to provide a full complement of genetic elements for replication. Sequences useful for selection in a suitable host can also be added to the annealing reaction.

For example, suppose that a 2000 base pair (b.p.) cDNA molecule is inserted into a lambda vector. One PCR product is created with a first primer that anneals 100 nucleotides "upstream" of the "left" insert/vector junction and a second primer that anneals to the nucleotides around position 1050 of the cDNA. A second PCR product is created with a first primer that anneals to the nucleotides around position 950 of the cDNA and a second primer that anneals 100 nucleotides "downstream" of the "right" insert/vector junction. While these two annealed PCR products alone are not sufficient to create a replication-competent plasmid, they can be mixed with one or more nucleic acids from a plasmid (a "plasmid backbone") to functionally fill-in the missing sequences and thereby create a complete plasmid having nucleotide sequences for replication and selection.

In this embodiment, because of the polarity of the strands, the plasmid backbone should have either 5' protruding single-stranded ends or 3' protruding single-stranded ends capable of annealing with the cDNA/vector PCR products. In the 2000 base pair cDNA insert example above, the 100 nucleotides of vector sequence contained on each PCR product can anneal with plasmid backbone sequences. When the two PCR products are denatured and then annealed, single-stranded DNA from each PCR product will anneal in the cDNA region from position 950 to position 1050. One form of annealed complex will involve the overlap of 3' ends, with nonoverlapping 5' ends. The other form of annealed complex will involve the overlap of 5' ends, with nonoverlapping 3' ends. The nonoverlapping ends will terminate in the 100 nucleotides of vector sequence that were incorporated into the PCR products. Thus, a plasmid backbone that is capable of annealing to two 3' or two 5' nonoverlapping ends is capable of annealing and forming a replication-competent complex.

The plasmid backbones are created by cleaving a plasmid at a site close to the insertion site of the cDNA clone, such that roughly 100 b.p. flanking the cleavage site are homologous to the 100 b.p. of protruding vector DNA on each PCR fragment. The double-stranded plasmid backbone fragment can then be treated with a 3' or 5' exonuclease (depending on which type of nonoverlapping ends are desired) so that 100 or more nucleotides are removed, creating single-stranded protruding ends. Such a modified plasmid backbone can then be annealed with the PCR fragments, comprising the insert DNA, and the final complex can either be transformed directly or treated with a polymerase to fill in single-stranded regions before transformation.

There are other methods for preparing the plasmid backbone prior to annealing with the primer extension products. Rather than treat with an exonuclease, the plasmid backbone can be prepared in two (or more) overlapping fragments having single-stranded nonoverlapping ends. Such ends can anneal to the nonoverlapping ends of the primer extension products. For example, two vector backbone and two insert/vector fragments can be created so that all four, when mixed, will anneal to form a replication-competent complex. Such complexes can be treated with a DNA polymerase to fill in single-stranded regions prior to transformation. Through the methods, plasmids, and kits described one skilled in the art can devise many plasmid backbone examples to be used with any particular extension product or PCR product involved.

EXAMPLE 1

Excision of pBluescript SK(−) Plasmid Vector Having an Insert from Lambda ZAPOI, Itself Having the Same Insert, Using f1 Origin-Specific and Insert-Specific PCR Primers The methods of the invention were used to excise the pBluescript SK(−) plasmid vector having a chloramphenicol-resistance gene as a DNA insert from the Lambda ZAP II lambda vector having the same insert. This Example demonstrates that the herein described methods could be used to simultaneously isolate and excise a plasmid vector having preselected DNA insert from a lambda vector having the same DNA insert.

The Lambda ZAP II lambda vector having a chloramphenicol-resistance gene as a DNA insert was prepared by ligating a segment of DNA comprising the $E.$ $coli$ promoter, $cam^r$ gene and translational stop codon into Lambda ZAP II ($cam^r$ insert). When the $cam^r$ insert is ligated into the pBluescript SK(−) plasmid vector, transformed into a chloramphenicol-sensitive $E.$ $coli$ and expressed, the transformed $E.$ $coli$ is resistant to chloramphenicol. Thus, the use of the $cam^r$ insert provides a convenient method of identifying $E.$ $coli$ colonies expressing the $cam^r$ insert. Adaptors comprising an EcoR I-compatible overhanging end and a Sma I-compatible blunt end were ligated to the $cam^r$ insert resulting in a $cam^r$ insert having EcoR I-compatible overhanging ends on each end of the insert. The $cam^r$ insert was ligated to a Lambda-ZAP® II vector predigested with EcoR I, packaged with lambda packaging extract and plated with $E.$ $coli$ cells to obtain individual plaques comprising the Lambda ZAP II vector. Individual plaques were screened to identify Lambda ZAP II vectors having the $cam^r$ insert. Thus, a Lambda ZAP II vector having a $cam^r$ gene DNA insert to be used as a template in practicing the invention was prepared.

Figure 1B:
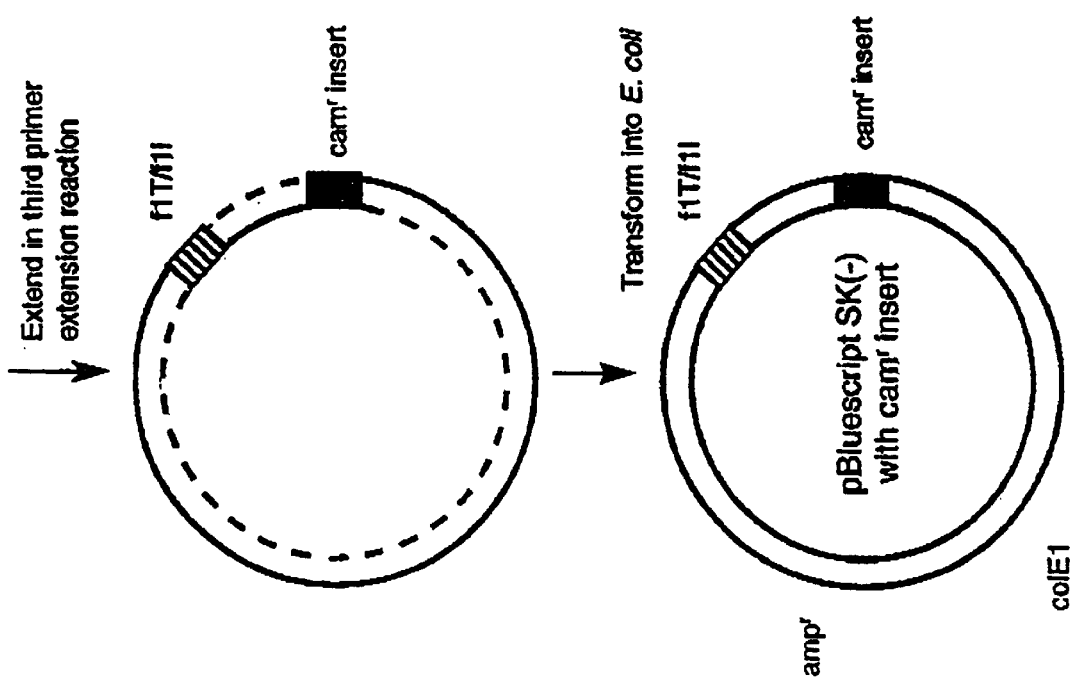
FIG. 1B depicts a primer extension repair reaction to create the substantially double-stranded plasmid containing insert, pBluescript® SK(−) with cam$^r$ insert. This repair reaction is optional. The double-stranded plasmid can also be formed in vivo, after transformation into an appropriate host.

Two different sets of PCR primers were used to excise the pBluescript SK(−) plasmid vector having a $cam^r$ insert from the Lambda ZAP II lambda vector having the same insert. One set, primers 078 and 079 (Table 1), was based upon the nucleotide sequence of the f1 origin sequence in the pBluescript SK(−) plasmid vector. The pBluescript SK(−) plasmid vector is embedded in the Lambda ZAP II lambda vector (FIGS. 1A and 1B). The other set of primers, primers 080 and 081 (Table 1), was based upon nucleotide sequences encoding a gene which confers chloramphenicol resistance (cam). The $cam^r$ gene had been ligated to the pBluescript SK(−) plasmid vector embedded in the Lambda ZAP II vector. The $cam^r$ gene insert was used for convenience in evaluating the methods described herein. The method is applicable to any other nucleic acid insert. The nucleic acid insert may be DNA, RNA or cDNA and may contain modified nucleotides such as nucleotides having a methyl group.

In Lambda ZAP II the f1 origin is divided into two parts, the f1 initiator and the f1 terminator. These parts have base pairs of homologous nucleotide sequence arranged as direct repeats relative to each other at each end of the plasmid replication sequences (the embedded pBluescript SK(−) plasmid vector (FIGS. 1A and 1B). The f1 phage origin of replication-specific primers (f1 origin-specific primers) are based upon this region of homology. Each of the f1 origin-specific primers anneal to nucleotide sequences in the f1 initiator and f1 terminator and thus amplify the pBluescript SK(−) plasmid vector sequences between the f1 initiator and f1 terminator.

The f1 origin-specific primers used in this Example are single-stranded, 34 bases in length, and are complementary. Following PCR, the first and second PCR products have 34 base pairs of homology at one end of each of the PCR products. When the first and second PCR products are denatured to form substantially single-stranded DNA, this region of homology provides 34 bases of single-stranded complementary DNA sequence, which anneal and form a suitable substrate for a polymerase extension reaction. The number of base pair overlap in the f1 origin-specific primers was arbitrarily selected and can vary between 0 and 84 base pairs. The number of base pairs of overlap must be sufficient to provide overlapping ends that can serve as a polymerase substrate.

The cam$^r$-specific primers are also single-stranded, 34 bases in length and complementary. Following PCR, the first and second PCR products have a second 34 base pairs of homology at the end of the PCR product opposite of the 34 base pairs of homology defined by the f1 origin-specific primers. When the first and second PCR products are denatured to form substantially single-stranded DNA, the two regions of homology provide 34 bases of single-stranded complementary DNA sequence, which anneal and form a suitable substrate for a polymerase extension reaction. The number of base pair overlap in the cam$^r$ insert-specific primers was arbitrarily selected and can vary between 10 and several hundreds or thousands of base pairs. The number of base pairs of overlap must be sufficient to provide overlapping ends that can serve as a polymerase substrate in the subsequent polymerase extension reaction.

TABLE 1

| Primer Description and Number | SEQ ID NO | Nucleotide Sequences (5' to 3') |
|---|---|---|
| cam$^r$ | | |
| 080 | 1 | CACATTCTTGCCCGCCTGATGAATGCTCATCCGG |
| 081 | 2 | CCGGATGAGCATTCATCAGGCGGGCAAGAATGT |
| f1 origin | | |
| 078 | 3 | CGTGGACTCCAACGTCAAAGGGCGAAAAACCGTC |
| 079 | 4 | GACGGTTTTTCGCCCTTTGACGTTGGAGTCCACG |

The PCR template, a Lambda ZAP II vector DNA having a cam$^r$ insert, was prepared as described herein. A first PCR product comprising a portion of the f1 terminator, the amp$^r$ gene, the E. coli colE1 origin, lacZ promoter and a portion of the cam$^r$ gene DNA insert was prepared using the f1 origin-specific primer 078 and the cam$^r$-specific primer 081. A second PCR product comprising the remaining portion of the cam$^r$ gene DNA insert and the f1 initiator was prepared using the cam$^r$-specific primer 080 and the f1 origin-specific primer 079.

The first and second PCR products were heat denatured to produce substantially single-stranded DNA. Any method of denaturation, including heat or treatment with alkali, is suitable as long as the method produces substantially single-stranded DNA in the regions of complementarity. The single-stranded DNA were combined and annealed at the regions of complementarity in the fl initiator and terminator and in the cam$^r$ gene DNA insert. The annealed PCR products are similar to an annealed primer and template and were a suitable substrate for polymerization in a primer extension reaction.

To perform the PCR, template DNA, primers, DNA polymerase, dNTPs and buffer were combined and the reaction was incubated at an appropriate temperature for a sufficient amount of time for polymerization to occur. The polymerization caused the annealed single-stranded DNA to become substantially double-stranded, circular DNA. The double-stranded DNA was then transformed into XL1-Blue E. coli competent cells to obtain isolated colonies containing the excised pBluescript SK(−) plasmid vector having a cam$^r$ insert.

Preparation of Lambda ZAP II Vector Having a Cam$^r$ Insert

The Lambda ZAP II lambda vector having a chloramphenicol-resistance gene (cam$^r$) as a DNA insert was prepared by ligating a segment of DNA comprising the E. coli promoter, cam$^r$ gene and translational stop codon (cam$^r$ insert; Stratagene; La Jolla, Calif.) into the Lambda ZAP II lambda vector. Adaptors comprising an EcoR Incompatible overhanging end and a Sma I-compatible blunt end (Stratagene; La Jolla, Calif.) were ligated to the blunt ends of the cam$^r$ insert (Stratagene; La Jolla, Calif.) resulting in a cam$^r$ insert having EcoR I-compatible overhanging ends on each end of the insert. Ligation conditions were as follows: 1 microgram (µg) cam$^r$ insert, 0.4 µg adaptors, 1× ligase buffer (1× ligase buffer is 50 mM Tris-HCl, pH 7.5; 7 mM MgCl$_2$; 1 mM DTT (dithiothreitol); 1 mM rATP) and 1 unit T4 DNA ligase (Stratagene; La Jolla, Calif.) were combined and incubated at 4° C. for 16 hours. Ligated cam$^r$ insert with adaptors were separated from unligated adaptors by the Qiagen PCR Purification kit (Qiagen; Chatsworth, Calif.). The 5' ends of the adaptors were then phosphorylated with T4 Polynucleotide Kinase. The kinase conditions were as follows: 0.5 µg cam$^r$ insert with adaptors, 1× ligase buffer, 10 mM rATP and 1 unit T4 Polynucleotide Kinase (Stratagene; La Jolla, Calif.) were combined and incubated at 37° C. for 45 minutes. The kinase reactions were then heated to 68° C. for 15 minutes to heat denature the kinase.

The cam$^r$ insert with kinased adaptors was ligated to Lambda ZAP® II Vector which was predigested with EcoR I and dephosphorylated with calf intestinal alkaline phosphatase (Stratagene; La Jolla, Calif.) as follows: 33 nanograms (ng) cam$^r$ insert with adaptors, 1 µg predigested Lambda ZAP II lambda vector, 1× ligase buffer and 1 unit T4 DNA ligase were combined and incubated at 14° C. for 1 hour. One tenth of the ligation reaction was packaged with Gigapack® III Gold lambda packaging extract following the manufacturers recommended procedures (Stratagene; La Jolla, Calif.) and plated with XL1-Blue E. coli cells to obtain individual plaques comprising the Lambda ZAP II vector. Individual plaques were screened by PCR with a vector-specific primer (T3 primer; SEQ ID NO: 25; 5'-AATTAACCCTCACTAAAGGG-3') and a cam$^r$ insert-specific primer (080) to identify Lambda ZAP II vectors having the cam$^r$ insert. The PCR was performed as follows: a small amount of plaque-containing material, 100 nanograms (ng) of each PCR primer, 2.5 units Taq DNA polymerase, 1× TaqPlus DNA polymerase reaction buffer [100 millimolar [mM] KCl, 100 mM [NH$_4$]SO$_4$, 200 mM tris (pH 8.8), 20 mM MgSO$_4$, 1% (volume/volume; v/v) Triton® X-100, 1 milligram [mg]/ml nuclease-free bovine serum albumin], and 200 µM each of dGTP, DATP, dTTP and dCTP. The PCR were overlaid with silicone oil and amplified as follows: one cycle of 93° C. for 5 minutes, 54° C. for 5 minutes and 72° C. for 2 minutes; thirty cycles of 93° C. for 1 minute, 54° C. for 1 minute, and 72° C. for 2 minutes; and one cycle of 72° C. for 10 minutes. The presence and molecular weight of each PCR product was determined by agarose gel electrophoresis. Two of the 20 colonies analyzed produced a PCR product corresponding to the cam$^r$ insert. Thus, a Lambda ZAP II vector having a cam$^r$ gene DNA insert to be used as a template in practicing the invention was prepared.

Preparation of First and Second PCR Products

To excise the pBluescript SK(−) plasmid vector having the cam$^r$ insert from the Lambda ZAP II lambda vector, a first and second PCR product were prepared by PCR amplification with f1 origin-specific and cam$^r$-specific primers and the template prepared above. The number of lambda phage particles containing the template DNA used in each PCR can vary between 1 and $10^{14}$. The only requirement is that at least one molecule of the first and of the second PCR product be produced. The overlap of PCR products generated with f1 origin-specific primers 078 and 079 was approximately 34 base pairs. The overlap of PCR products generated with cam$^r$-specific primers 080 and 081 was approximately 34 base pairs. The number of base pairs of overlap is based upon the length of the homologous sequence as defined by the PCR primers and was arbitrarily selected. The minimum number of base pairs of overlap would be approximately 10 base pairs. The maximum number of base pairs of overlap would be several hundred base pairs.

First PCR products were amplified with f1 origin- and cam$^r$ insert-specific primers 078 and 081, respectively. The second PCR products were amplified with f1 origin- and cam$^r$ insert-specific primers 079 and 080, respectively. The nucleotide sequence of these primers and their corresponding SEQ ID NOs are given in Table 1. Approximately 2.2×105 phage particles, 200 nanograms (ng) of each PCR primer, 2.5 units TaqPlus DNA polymerase, 1× TaqPlus DNA polymerase reaction buffer and 200 μM each of dGTP, dATP, dTTP and dCTP were combined. The PCR were overlaid with silicone oil (Sigma; St. Louis, Mo.) and amplified as follows: one cycle of 93° C. for 5 minutes, 54° C. for 5 minutes and 72° C. for 7 minutes; thirty cycles of 93° C. for 1 minute, 54° C. for 1 minute and 72° C. for 7 minutes; and one cycle of 72° C. for 10 minutes. The presence and molecular weight of each PCR product was verified by agarose gel electrophoresis.

Preparation, Transformation and Selection of Extension Products

First and second PCR products were then combined to generate the excised pBluescipt SK(−) vector having a cam$^r$ insert. First PCR products generated with primer pairs 078/081 and second PCR products generated with primer pairs 0791080 were mixed, denatured and annealed. Ten μl of each PCR, 2.5 units TaqPlus DNA polymerase Long, 1× TaqPlus DNA polymerase reaction buffer and 200 μM each of dGTP, dATP, dTTP and dCTP were combined. The extension reactions were overlaid with silicone oil and extended as follows: one cycle of 68° C. for 10 minutes, 93° C. for 5 minutes and 68° C. for 60 minutes. Ten μl of the extension products were transformed into XL1-Blue MRF' Epicurian Coli® supercompetent cells (Stratagene; La Jolla, Calif.) following the manufacturer's protocol, plated on Luria Broth (LB) plates containing 100 μg/ml ampicillin, and incubated at 37° C. to select for *E. coli* colonies containing the extension products. The presence and function of the cam$^r$ insert was verified by transferring the colonies containing the extension products to LB plates containing 34 μg/ml chloramphenicol and incubating at 37° C. to select for *E. coli* colonies expressing the cam$^r$ insert. Those colonies expressing the cam$^r$ insert contain extension products representing the pBluescript SK(−) plasmid vector having a cam$^r$ insert which has been excised from the Lambda ZAP II lambda vector having the same cam$^r$ insert.

Thus, a Lambda ZAP II lambda vector having a cam$^r$ insert has been excised to form a pBluescript SK(−) plasmid vector having the same cam$^r$ insert using the methods of this invention. These methods were then applied to the simultaneous isolation and excision of pBluescript SK(−) plasmid vectors having a preselected DNA insert from a library of Lambda ZAP II lambda vectors having different DNA inserts.

EXAMPLE 2

Isolation and Excision of Rat NCAM cDNA Clones from a Rat Brain cDNA Library Using Human NCAM-Specific and f1 Origin-Specific PCR Primers The methods of the invention were used to isolate and excise Lambda ZAP II vectors having cDNA inserts encoding rat NCAM from a rat brain cDNA library. In this method, the plasmid portion of the Lambda ZAP II lambda vector with rat NCAM cDNA insert was excised to form a pBluescript SK(−) plasmid vector with the same rat NCAM cDNA insert.

The NCAM-specific PCR primers are derived from the human NCAM nucleotide sequence. While the nucleotide sequence of rat and human NCAM are not identical, there is sufficient homology between the human-specific PCR primers and rat NCAM cDNA insert to practice the invention. A comparison of the human-specific PCR primers and rat NCAM cDNA sequence is given in Table 2.

TABLE 2

| Identity of nucleotide sequence | Nucleotide position in rat NCAM sequence[1] | SEQ ID NO | Nucleotide sequence (5' to 3') |
|---|---|---|---|
| 152 Primer | 2648–2678 | 5 | CTACGGGCCGCTTCTCGGGCTCCGTCAGTGG |
| Rat NCAM | 2648–2678 | 6 | -----A-A-C------------T-------- |
| NCAM2 Primer | 3002–3025 | 7 | GTGCAACAAAGGGACCCTTTCTAT |
| Rat NCAM | 3002–3025 | 8 | ------------AG---------G |
| 151 Primer | 2648–2678 | 9 | CCACTGACGGAGCCCGAGAAGCGGCCCGTAG |

TABLE 2-continued

| Identity of nucleotide sequence | Nucleotide position in rat NCAM sequence[1] | SEQ ID NO | Nucleotide sequence (5' to 3') |
|---|---|---|---|
| Rat NCAM | 2648–2678 | 10 | --------A------------G-T-T----- |
| 167 Primer | 2537–2558 | 11 | GCCGCCTTCTCGAAAGATGAG |
| Rat NCAM | 2537–2558 | 12 | --T-T---------------- |

The "-" indicates the nucleotide is the same as in sequence immediately above.
[1]GenBank Accession Number X06564

The PCR templates were a rat brain cDNA library comprising Lambda ZAP II vectors having different rat brain cDNA inserts (Stratagene; La Jolla, Calif.). The vector DNA were contained within lambda phage particles and were released from the particles by heat denaturation of the particles. Release of the vector DNA allows the DNA to be used as a template in PCR. The cDNA library was a mixture of lambda phage particles and E. coli lysate comprising E. coli chromosomal DNA. As this DNA may also serve as primers and templates in the subsequent PCR reactions and compete with the desired primers and templates for PCR reagents and potentially result in undesired PCR products, at least a portion of the E. coli DNA was removed by differential precipitation of the phage particles with polyethylene glycol prior to the PCR. While the removal of the E coli chromosomal DNA may improve the results in this method, the invention can be practiced without removal of this DNA.

A first PCR product comprising a portion of the f1 terminator, the amp$^r$ gene, the E coli colE1 origin, lacZ promoter sequences and a part of the rat NCAM cDNA insert was prepared using the f1 origin-specific primer 078 and one of the human-specific NCAM primers 152 or NCAM2. The f1 terminator, amp$^r$ gene and E. coli colE1 origin nucleotide sequences were derived from the embedded pBluescript SK(–) vector. A second PCR product comprising the remaining part of the rat NCAM cDNA insert and a part of the f1 initiator was prepared using one of the human NCAM-specific primers 151 or 167 and the f1 origin-specific primer 079. The part of the f1 initiator was derived from the embedded pBluescript SK(–) vector.

The first and second PCR products were denatured to produce substantially single-stranded DNA. The PCR products can be denatured by any method, including heat or alkali treatment. The only requirement is the production of substantially single-stranded DNA. The single-stranded DNA were combined and annealed at regions of complementarity in the f1 initiator and terminator and in the rat NCAM cDNA insert. The annealed PCR products are similar to an annealed primer and template and were a suitable substrate for polymerization. A DNA polymerase, dNTPs and buffer were added and the reaction was incubated at an appropriate temperature for a sufficient amount of time for polymerization to occur. The polymerizaton caused the annealed single-stranded DNA to become substantially double-stranded DNA. The double-stranded DNA was then transformed into XL1-Blue E coli competent cells to obtain colonies containing the excised pBluescript SK(–) vector having a rat NCAM cDNA insert.

The identity of the isolated and excised rat brain cDNA inserts were confirmed by comparison to a previously published rat NCAM nucleotide sequence (GenBank Accession Number X06564).

Removal of E. coli Chromosomal DNA

To separate E. coli chromosomal DNA from the lambda phage particles comprising the rat brain cDNA library, the mixture was differentially precipitated with polyethylene glycol. Five hundred microliters ($\mu$l) of the mixture (approximately $3.2 \times 10^{10}$ phage particles) was combined with an equal volume of 2 molar (M) NaCl and 20% (weight/volume; wN) $PEG_{8000}$ and incubated on ice for 1 hour. The mixture was centrifuged at 14,000× g for 10 minutes, the supernatant containing the E. coli chromosomal DNA removed and discarded, the mixture was recentrifuged at 14,000× g for 30 seconds and the remaining supernatant removed. The pellet, comprising the lambda phage particles, was resuspended in 100 $\mu$l of suspension medium (SM) Sambrook, J. et al., Molecular Cloning, A Laboratory Manual, 2d Ed. (1989).

Preparation of First and Second PCR Products

To isolate and excise the pBluescript SK (–) plasmid vector having a rat NCAM cDNA insert from the library of Lambda ZAP II lambda vectors having different rat brain cDNA inserts, first and second PCR products were prepared by PCR amplification with human NCAM- and f1 origin-specific primers. A lambda phage library was the source of Lambda ZAP II vectors having the rat NCAM insert templates. More than one combination of human-specific NCAM primers in separate PCR reactions were used to generate the first and second PCR products. The use of more than one combination of primers resulted in the preparation of PCR products containing rat NCAM cDNA inserts of different lengths and with different 5' and 3' ends. The overlap of the first and second PCR products prepared with human-specific NCAM primer pairs 078/152 and 079/167, respectively, was approximately 139 base pairs. The overlap of first and second PCR products prepared with human-specific NCAM primer pairs 078/152 and 0791167 respectively, was approximately 469 base pairs. The given number of base pairs of overlap is based upon the rat NCAM cDNA sequence given in GenBank Accession Number X06564. Rat NCAM cDNA is know to be alternatively spliced which causes variations in the length of the cDNA and thus affects the number of base pair overlap. The number of base pairs of overlap described herein were arbitrarily selected. The minimum number of base pairs of overlap would be approximately 10 base pairs. The maximum number of base pairs of overlap would correspond to the length of the cDNA insert and any desired vector sequence.

First PCR products were prepared with f1 origin-specific and human NCAM-specific primer pairs 078/152 and 078/NCAM2. The second PCR products were amplified with f1 origin- and human NCAM-specific primer pairs 079/151 and 079/167. The nucleotide sequence of these primers and their corresponding SEQ ID NOs are given in Table 3. Approximately $1.2 \times 10^8$ phage particles, 200 nanograms (ng) of each PCR primer, 2.5 units TaqPlus™ DNA polymerase Long (Stratagene; La Jolla, Calif.), 1× TaqPlus DNA polymerase reaction buffer, and 200 μM each of dGTP, DATP, dTTP and dCTP. The PCR were overlaid with silicone oil (Sigma; St. Louis, Mo.) and amplified as follows: one cycle of 93° C. for 5 minutes, 54° C. for 5 minutes and 72° C. for 10 minutes; thirty cycles of 93° C. for 1 minute, 54° C. for 1 minute, and 72° C. for 10 minutes; and one cycle of 72° C. for 10 minutes. The presence of each PCR product was determined by agarose gel electrophoresis.

TABLE 3

| | SEQ ID NO | Nucleotide Sequence (5' to 3') |
|---|---|---|
| First PCR Product Primers | | |
| f1 origin | | |
| 078 | 3 | CGTGGACTCCAACGTCAAAGGGCGAAAAACCGTC |
| Human | | |
| 152 | 13 | CTACGGGCCGCTTCGGGCTCCGTCAGTGG |
| NCAM2 | 14 | GTGCAACAAAGGGACCCTTTCTAT |
| Second PCR Product Primers | | |
| f1 origin | | |
| 079 | 4 | GACGGTTTTTCGCCCTTTGACGTTGGAGTCCACG |
| Human | | |
| 151 | 15 | CCACTGACGGAGCCCGAGAAGCGGCCCGTAG |
| 167 | 16 | GCCGCCTTCTCGAAAGATGAG |

Preparation, Transformation, and Selection of Extension Products

First and second PCR products were mixed, denatured and annealed in all possible combinations of first and second PCR products. First PCR products prepared with primer pairs 078/152 and second PCR products prepared with primer pairs 079/167 were mixed, denatured and annealed. PCR products prepared with primer pairs 078/152 and 079/151; 078/NCAM2 and 079/167; and 078/NCAM2 and 079/051 were similarly combined. Extension products were prepared by combining 10 μl of each PCR, 2.5 units TaqPlus DNA polymerase Long, 1× TaqPlus DNA polymerase reaction buffer and 200 μM each of dGTP, DATP, dTTP and dCTP. The PCR were overlaid with silicone oil and extended as follows: one cycle of 93° C. for 5 minutes and 68° C. for 60 minutes. Ten μl of the extension products were transformed into XL1-Blue MRF' Epicurian Coli® supercompetent cells (Stratagene; La Jolla, Calif.), following the manufacturer's protocol, plated on Luria Broth plates containing 100 μg/ml ampicillin, and incubated at 37° C. to select for E. coli colonies containing the extension products. The extension products represent the pbluescript SK(−) plasmid vector having the same rat brain cDNA insert, which has been excised from the Lambda ZAP II lambda vector having a rat brain cDNA insert.

Colonies containing the pBluescript SK(−) plasmid vector having a rat brain cDNA insert were identified by PCR with the vector-specific T3 (SEQ ID NO: 25; 5'-AATTAACCCTCACTAAAGGG-3') and T7 primers (SEQ ID NO: 26, 5'-GTAATACGACTCACTATAGGGC-3') (Stratagene; La Jolla, Calif.). A small amount of colony material, 100 nanograms (ng) of each PCR primer, 2.5 units TaqPlus DNA polymerase Long, 1× TaqPlus DNA polymerase reaction buffer and 200 μM each of dGTP, DATP, dTTP and dCTP were combined in each PCR. The PCR were overlaid with silicone oil and amplified as follows: one cycle of 93° C. for 5 minutes, 54° C. for 5 minutes and 72° C. for 2 minutes; thirty cycles of 93° C. for 1 minute, 54° C. for 1 minute, and 72° C. for 2 minutes; and one cycle of 72° C. for 10 minutes. The presence and molecular weight of each PCR product was determined by agarose gel electrophoresis. Nine of the 30 colonies analyzed produced a PCR product, which corresponded to the rat brain cDNA insert, under the conditions used.

Identification of cDNA Insert

The partial nucleotide sequences of the rat brain cDNA inserts from 5 of the colonies were determined by isolating plasmid DNA using Qiagen Plasmid Maxi Kit (Qiagen; Chatsworth, Calif.) and determining the nucleotide sequence by the Sanger dideoxy method (Sanger, F., et al. P.N.A.S. 74:5463–67 (1977). The T3 and T7 primers were used in separate sequencing reactions. The rat NCAM clones examined were generated from the overlap of first (078/152) and second (0791167) PCR products and from first (078/NCAM2) and second (079/167) PCR products.

The nucleotide sequences of all the clones examined were highly homologous to that of the rat NCAM sequence given in GenBank Accession Number X06564. The rat NCAM clones isolated and their respective designations and 5' and 3' nucleotide positions corresponding to the rat NCAM cDNA (GenBank Accession Number X06564) are given in Table 4. The 3' nucleotide position 3170 corresponds to the last nucleotide before the addition of poly A nucleotides.

TABLE 4

| RAT NCAM | Nucleotide Position Corresponding to Rat NCAM cDNA (X06564) | |
|---|---|---|
| Clone Desigation | 5' nucleotide position | 3' nucleotide position |
| R1H | 1938 | 3170 |
| R1I | 960 | 3170 |
| R1F | 2289 | 3170 |
| R2D | 1300 | 3170 |
| R2I | 929 | 2958 |

The nucleotide sequence of the isolated and excised clones correspond to the previously published rat NCAM sequence. Thus, Lambda ZAP® II lambda vectors having rat NCAM cDNA inserts have been isolated and excised to form pBluescript plasmid vectors having the same rat NCAM cDNA inserts using the methods of this invention. To isolate and excise the rat NCAM clones, PCR primers of <100% homology to rat NCAM cDNA were used. These results demonstrate that this method can be used to isolate and excise clones having <100% homology to the PCR primers used and, thus, to identify similar, related, or other non-identical nucleic acid species from a nucleic acid library. The use of <100% homologous primers can also result in the introduction of site-specific mutations, insertions, or deletions.

EXAMPLE 3

Isolation and Excision of Human Actin cDNAs from a Human Brain cDNA Library Using Human Actin-Specific and f1 Origin-Specific PCR Primers The methods of the invention were used to isolate and excise Lambda ZAP II vectors having cDNA inserts encoding human actin from a human brain cDNA library. In this method, the plasmid portion of the Lambda ZAP II lambda vector with human actin cDNA insert was excised to directly form a pBluescript SK(−) plasmid vector with the same human cDNA insert. In this way, human β- and γ-actin clones were isolated and excised using β-actin-specific PCR primers, further demonstrating that the methods described herein can be used to isolate and excise related or structurally similar cones.

Two sets of PCR primers were used to prepare first and second PCR products. The first set was based upon the human β-actin nucleotide sequence (GenBank Accession Number M10277).

The second set was based upon the f1 origin but are not the same primers as those used in Examples 1 and 2. The set of primers was also based on the nucleotide sequences of the f1 origin but anneal to different nucleotides sequences in the f1 origin and thus contain different nucleotide sequence of the f1 origin. When the first and second PCR products are annealed, they generate a 81 base pair overlap of f1 origin-specific sequences. The PCR templates were a human brain cDNA library comprising Lambda ZAP II vectors having different human brain cDNA inserts (Stratagene; La Jolla, Calif.). The phage particles containing the vector DNA were partially purified by differential precipitation as described in Example 2.

A first PCR product comprising a portion of the f1 terminator, the amp$^r$ gene, the *E. coli* colE1 origin, lacZ promoter sequences and a part of the human actin cDNA insert was prepared using the f1 origin-specific primer 142 and one of the human-specific β-actin primers 962 (Table 5). The f1 terminator, amp$^r$ gene and *E. coli* colE1 origin nucleotide sequences were derived from the embedded pBluescript SK(−) vector. A second PCR product comprising the remaining part of the human β-actin cDNA insert and a part of the f1 initiator was prepared using one of the human β-actin-specific primers 960 or 961 (Table 5) and the f1 origin-specific primer 141. The part of the f1 initiator was derived from the embedded pBluescript SK(−) vector.

The first and second PCR products were combined, denatured, annealed, extended and transformed into *E. coli* as described in Example 2.

The identity of the isolated and excised human brain cDNA inserts were confirmed by comparison to previously published human β- and γ-actin sequences (GenBank Accession Numbers M10277 and X04098, respectively).

Preparation of First and Second PCR Products

To isolate and excise the pBluescript SK (−) plasmid vector having a human actin cDNA insert from the library of Lambda ZAP II lambda vectors having different human brain cDNA inserts, first and second PCR products were prepared by PCR amplification with human β-actin- and f1 origin-specific primers. A lambda phage library was the source of Lambda ZAP II vectors having the human brain cDNA insert templates. More than one combination of human-specific primers were used to generate the first and second PCR products. The human β-actin-specific primers were based upon the nucleotide sequences given in GenBank Accession Number M10277. The nucleotide positions given in Table 5 correspond to the M10277 nucleotide sequence. The use of more than one combination of primers resulted in the preparation of PCR products containing human β-actin cDNA inserts of different lengths and with different 5' and 3' ends. The overlap of first and second PCR products prepared with human-specific Mactin primer pairs 142/962 and 1411961 was approximately 740 base pairs.

The overlap of first and second PCR products prepared with human-specific β-actin primer pairs 142/960 and 141/963 was approximately 32 base pairs. The given number of base pairs of overlap is based upon the human Mactin nucleotide sequence given in GenBank Accession Number M10277. The number of base pairs of overlap described herein were arbitrarily selected. The minimum number of base pairs of overlap would be approximately 10 base pairs. The maximum number of base pairs of overlap corresponds to the length of the cDNA insert and the vector sequence. In addition, the human-specific β-actin primers were designed to have high homology to and thus anneal to γ-actin cDNA. This primer design resulted in the preparation of PCR products comprising γ-actin cDNA as well as β-actin cDNA. Thus, the methods of this invention can be used to isolate and excise preselected cDNA sequences as well as related cDNA sequences having homology to the primers used.

First PCR products were prepared with f1 origin- and human β-actin-specific primer pairs 142/961 and 142/963. The second PCR products were amplified with f1 origin- and human β-actin-specific primer pairs 141/962 and 141/960. Approximately 1.2×11Y phage particles, 200 nanograms (ng) of each PCR primer, 2.5 units cloned Pfu DNA polymerase (Stratagene; La Jolla, Calif.), 1× cloned Pfu DNA polymerase reaction buffer (1×=100 millimolar [mM] KCl, 100 mM [NH4]SO4, 200 mM tris [pH 8.8], 20 mM MgSO4, 1% [volume/volume; v/v] Tritone X-100, 1 milligram [mg]/ml nuclease-free bovine serum albumin), 1 μl of a 1:500 dilution of a PCR additive PEF (U.S. patent application Ser. No. 08/822,774, filed Mar. 21, 1997, specifically incorporated herein by reference), 200 μM each of dGTP, DATP, dTTP and dCTP and 1 unit PerfectMatch® Polymerase Enhancer (U.S. Pat. No. 5,449,603; Stratagene; La Jolla, Calif.). The addition of PEF is optional. The PCR reaction solutions were overlaid with silicone oil (Sigma, St. Louis, Mo.). The human M-actin PCR protocol was as follows: one cycle of 93° C. for 5 minutes, 54° C. for 5 minutes and 68° C. for 2 minutes; thirty cycles of 93° C. for 1 minute, 54° C. for 1 minute, and 68° C. for 2 minutes; and one cycle of 68° C. for 10 minutes. The presence of each PCR product was determined by agarose gel electrophoresis.

TABLE 5

| | SEQ ID NO | Nucleotide Sequence (5' to 3') |
|---|---|---|
| | First PCR Product Primers | |
| f1 origin | | |
| 142 | 17 | GCCATCGCCCTGATAGACGGTTTTTCGCCCTTTG |
| Human β-actin | | |
| 961 | 18 | CTCATGAAGATCCTCACCGAGCCGGCTACAG |
| 963 | 22 | CTGTAGCCGCGCTCGGTGAGGATCTTCATGAG |

TABLE 5-continued

| | SEQ ID NO | Nucleotide Sequence (5' to 3') |
|---|---|---|
| Second PCR Product Primers | | |
| f1 origin | | |
| 141 | 19 | CCAGTTTGGAACAAGAGTCCACTATTAAGAACG |
| Human β-actin | | |
| 960 | 21 | ATGGATGATGATATCGCCGCGCTCGTCGTCG |
| 962 | 20 | GCCGGACTCGTCATACTCCTGCTTGCTGATC |

Preparation, Transformation, and Selection of Extension Products

First and second PCR products were mixed, denatured, annealed, extended and transformed into E. coli to select for extension products. First PCR products prepared with primer pairs 142/963 and second PCR products prepared with primer pairs 141/961 were mixed, denatured and annealed. First PCR products 141/963 and second PCR products 142/960 were similarly combined. Extension products were prepared by combining 10 μl of each PCR, 2.5 units cloned Pfu DNA polymerase, 1× cloned Pfu DNA polymerase reaction buffer and 200 μM each of dGTP, dATP, dTTP and dCTP. The extension reactions were overlaid with silicone oil and extended as follows: one cycle of 93° C. for 5 minutes and 68° C. for 60 minutes. Ten μl of the extension products were transformed into XL1-Blue MRF' Epicurian Coli® supercompetent cells (Stratagene, La Jolla, Calif.) following the manufacturer's protocol, plated on Luria Broth plates containing 100 μg/ml ampicillin (Sambrook, J. et al., Molecular Cloning, A Laboratory Manual, 2d Ed. (1989)), and incubated at 37° C. to select for E. coli colonies containing the extension products. The extension products represent the pBluescript SK(−) plasmid vector having the either a human β- or γ-actin cDNA insert which has been excised from the Lambda ZAP II lambda vector having the same human cDNA insert.

Identification of cDNA Insert

The partial nucleotide sequences of the human β- and γ-actin cDNA inserts were determined by isolating plasmid DNA using ClearCut™ Miniprep Kit (Stratagene; La Jolla, Calif.) and determining the nucleotide sequence by the Sanger dideoxy method (Sanger, F., et al. PNAS 74:5463–5467 (1977)). The T3 (SEQ ID NO: 25) and T7 (SEQ ID NO: 26) primers were used in separate sequencing reactions. The human β- and γ-actin done designations and 5' and 3' nucleotide positions corresponding to the human β- and γ-actin cDNA given in GenBank Accession Numbers, in parentheses, are given in Table 6. Nucleotide position 1761 is the last nucleotide prior to the addition of poly A nucleotides.

TABLE 6

| Human actin clone designation | Nucleotide position corresponding to human β-actin cDNA (M10277) | | Nucleotide position corresponding to human γ-actin cDNA (X04098) | |
|---|---|---|---|---|
| | 5' nucleotide position | 3' nucleotide position | 5' nucleotide position | 3' nucleotide position |
| 1C | 472 | 1761 | | |
| 1E | 410 | 1761 | | |
| 1B | | | 272 | 1761 |

The nucleotide sequence of the isolated and excised clones correspond to the previously published human β- and γ-actin sequences. Thus, Lambda ZAP II lambda vectors having human β- and γ-actin cDNA inserts have been isolated and excised to form pBluescript plasmid vectors having the same cDNA inserts using the methods of this invention. Thus, the methods of this invention can be used to isolate and excise pbluescript SK(−) plasmid vectors having homologous but not identical cDNA inserts from Lambda ZAP II lambda vectors having different cDNA inserts.

EXAMPLE 4

Nucleotide Sequence-Independent Ligation of Nucleic Acids

The methods of the invention were used to ligate nucleotide sequences at preselected nucleotide sequences. In this method, a nucleotide sequence encoding a 0lactamase gene was ligated to a pCR-Script® Cam SK(+) vector at a preselected nucleotide sequence. This method of ligation is independent of nucleotide sequence and therefore is not dependent upon the presence or absence of restriction enzyme recognition sites. The method can be used to join two or more nucleotide sequences at any preselected sequences.

Two different sets of pCRScript Cam SK(+)- and amp$^r$-specific PCR primers were used. Each primer had priming and non-priming regions. The priming region was on the 3' end of the primer, was 20 bases in length and had homology to a first nucleotide sequence. The non-priming region was on the 5' end of the primer, was 10 bases in length and had homology to a second nucleotide sequence. The number of nucleotides in the priming and non-priming regions were arbitrarily selected and can be any number of nucleotides which results in the desired activity. One set of primers had priming regions with homology to the amp$^r$ gene and non-priming regions with homology to the pCR-Script Cam SK(+) plasmid vector. The second set of primers had priming regions with homology to the pCRScript Cam SK(+) plasmid vector and non-priming regions with homology to the amp$^r$ gene. Primers having priming and non-priming regions, wherein the priming regions had homology to a first nucleotide sequence and the non-priming regions had homology to a second nucleotide sequence, were used in order to introduce regions of homology to the second nucleotide sequence onto the ends of a first nucleotide sequence. The nucleotide sequence, priming region homology, non-priming region homology, and SEQ ID NOs of each primer is given in Table 7.

TABLE 7

| Primer | SEQ ID NO: | Priming Region Homology | Non-priming Region Homology | Nucleotide Sequence (5' to 3') |
| --- | --- | --- | --- | --- |
| 147 | 21 | amp$^r$ | T3 promoter | CACTAAAGGGGTGCGCGGAACCCCTATTTG |
| 148 | 22 | amp$^r$ | T7 promoter | GCGTAATACGGAGTAAACTTGGTCTGACAG |
| 149 | 23 | T3 promoter | amp$^r$ | TTCCGCGCACCCCTTTAGTGAGGGTTAATT |
| 150 | 24 | T7 promoter | amp$^r$ | AAGTTTACTCCGTATTACGCGCGCTCACTG |

Non-priming regions are indicated in bold.

The PCR templates were pCR-Script Cam SK(+) (Stratagene; La Jolla, Calif.) and a segment of DNA comprising the *E. coli* promoter, amp$^r$ gene and translational stop codon (amp$^r$ insert; Stratagene; La Jolla, Calif.).

Preparation of First and Second PCR Products

A first PCR product comprising (from 5' to 3') 10 base pairs having homology to the T3 promoter nucleotide sequences of pCRScript Cam SK(+), the amp$^r$ insert, and 10 base pairs having homology to the T7 promoter nucleotide sequences of pCRScript Cam SK(+) was prepared using the amp$^r$ insert-specific primers 147 and 148 with the amp$^r$ insert as the template. The regions having homology to pCR-Script Cam SK(+) were derived from the non-priming regions of primers 147 and 148. A second PCR product comprising (from 5' to 3') 10 base pairs having homology to the 5' end of the amp$^r$ insert, the pCRScript Cam SK(+) vector from the T3 promoter to the T7 promoter, and 10 base pairs having homology to the 3' end of the amp$^r$ insert was prepared using the pCR-Script Cam SK(+) vector-specific primers 149 and 150 with the pCR-Script Cam SK(+) vector as the template. The regions having homology to the amp$^r$ insert were derived from the non-priming regions of primers 149 and 150.

The first and second PCR products were heat denatured to produce substantially single-stranded DNA. The single-stranded DNA were combined and annealed at regions of complementarity in the T3 promoter and amp$^r$ insert and in the T7 promoter and amp$^r$ insert. The annealed PCR products are similar to an annealed primer and template and were a suitable substrate in an extension reaction. A DNA polymerase, dNTPs and buffer were added and the reaction was incubated at an appropriate temperature for a sufficient amount of time for extension to occur. The extension caused the annealed single-stranded DNA to become substantially double-stranded DNA. The double-stranded DNA was then transformed into XL1-Blue *E. coli* competent cells and plated on media containing chloramphenicol to select for colonies containing the pCR-Script Cam SK(+) vector. Colonies containing the ligated amp$^r$ insert and pCR-Script Cam SK(+) vector were then selected by transferring the transformed *E. coli* cells onto media containing ampicillin.

To ligate the amp$^r$ insert and pCR-Script Cam SK(+) vector at preselected nucleotide sequences, a first and second PCR product were prepared by PCR amplification with primers having priming and nonpriming regions and either pCR-Script Cam SK(+) of the amp$^r$ insert as DNA templates. The overlap of PCR products on each end was approximately 30 base pairs. The number of base pairs of overlap described herein were arbitrarily selected. The minimum number of base pairs of overlap would be approximately 10 base pairs. The maximum number of base pairs of overlap would correspond to the length of the an insert.

First PCR products were amplified with amp$^r$-priming primers 147 and 148 with the amp$^r$ insert template. The second PCR products were amplified with pCR-Script CAM SK(+) vector priming primers 149 and 150. The nucleotide sequence of these primers and their corresponding SEQ ID NO: are given in Table 7. Approximately 100 ng of each template, 200 ng of each PCR primer, 2.5 units native Pfu DNA polymerase (Stratagene; La Jolla, Calif.), 1× native Pfu DNA polymerase reaction buffer [100 mM KCl, 60 mM (NH$_4$)$_2$SO$_4$, 200 mM tris-HCl (pH 8.0), 20 mM MgCl$_2$, 1% (v/v) Triton X-100 and 1000 µg/ml bovine serum albumin] and 200 µM each of dGTP, dATP, dTTP and dCTP were combined. The PCR were overlaid with silicone oil (Sigma, St. Louis, Mo.) and amplified as follows: one cycle of 95° C. for 5 minutes and 60° C. for 10 minutes; thirty cycles of 95° C. for 1 minute and 60° C. for 10 minutes; and one cycle of 60° C. for 10 minutes. The presence of each PCR product was determined by agarose gel electrophoresis.

Preparation, Transformation and Selection of Extension Products

First and second PCR products were mixed, denatured, annealed and extended to generate extension products of the ligated amp$^r$ insert and pCR-Script Cam SK(+). First PCR products generated with primers 148 and 149 and second PCR products generated with primers 149 and 150 were mixed, denatured and annealed. Ten µl of each PCR, 2.5 units Pfu DNA polymerase, 1x Pfu 15; DNA polymerase reaction buffer and 0.2 mM each of dGTP, dATP, dTTP and dCTP were combined. The extension reactions were overlaid with silicone oil and extended as follows: one cycle of 95° C. for 5 minutes and 68° C. for 60 minutes. Ten µl of the extension products were transformed into XLI-Blue MRF' Epicurian Coli® supercompetent cells (Stratagene; La Jolla, Calif.) following the manufacturer's protocol, plated on Luria Broth plates containing 34 µg/ml chloramphenicol, and incubated at 37° C. to select for *E. coli* colonies containing the pCR-Script Cam SK(+) plasmid vector. The colonies were then transferred to LB plates containing 100 µg/ml ampicillin to select for *E. coli* colonies containing the ligated amp$^r$ insert and pCRScript Cam SK(+) plasmid vector.

The selection of *E. coli* colonies expressing genes conferring resistance to the chloramphenicol and ampicillin demonstrates that these colonies contain the ligated amp$^r$ insert and pCR-Script Cam SK(+) vector. Thus, using the methods of this invention, two nucleotide sequences have been ligated at preselected nucleotide sequences to generate a replication-competent form. The ligation is independent of the nucleotide sequence and independent of the presence or absence of restriction endonuclease recognition sites.

In summary, the methods of this invention were used to isolate desired nucleic acid species in a form that was replicated in a host cell or organism. As described in Examples 2 and 3, the desired nucleic acid species were isolated from a variety of nucleic acid libraries. The oligonucleotide primers used in this invention were homologous to the desired nucleic acid species and had sufficient homology to other related nucleic acid species to simultaneously isolate those species, as described in Example 3. In addition, oligonucleotide primers having homology to a desired nucleic acid of one animal species were used to isolate a desired nucleic acid from a different animal species, as described in Example 2. While single pairs of oligonucleotide primers having homology to the desired nucleic acid and single nucleic acid libraries were used in the Examples given herein, one of skill in the art will appreciate that more than one or more pairs of oligonucleotide primers can be used simultaneously to screen one or more nucleic acid libraries.

Several different polymerases and combinations thereof were used to isolate and excise the desired nucleic acid species from nucleic acid libraries. It was demonstrated that either strand displacing or non-strand displacing conditions could be used to prepare the first and second PCR products. A non-strand displacing condition was used to extend the first and second PCR products to generate a form that can be replicated in a host cell or organism. In addition, several additives (such as Perfect Match and PEF), which are useful in practicing this invention, were examined. While the use of additives is not necessary in practicing this invention, their use may enhance the desired results.

The method is further useful in the ligation of two or more nucleic acids at a preselected nucleotide sequence wherein the ligation is independent of the nucleotide sequence of the ligated nucleic acids. This method is particularly advantageous since it can be used in the absence of one or more convenient restriction endonuclease recognition sites within the nucleic acid sequence when it is undesirable to introduce additional nucleotide sequences into the ligated nucleic acids.

Although the invention has been described and illustrated in detail, it is to be clearly understood that the description is merely illustrative of embodiments of the invention. One skilled in the art can produce many other embodiments without departing from the scope of this invention. The description or examples are not to be taken as a limitation on the scope of this invention. The spirit and scope of the invention are to be limited only by the terms of the appended claims.

I claim:

1. A method for producing a vector comprising a desired nucleic acid insert from a sample comprising a plurality of vectors, the method comprising:

generating first and second extension products from first and second primers annealed to a vector in the sample, wherein the vector comprises a desired nucleic acid insert, wherein the first and second primers anneal to complementary strands of the vector comprising the desired nucleic acid insert, wherein one or both of the first or second primers comprise a nucleic acid sequence found in the desired nucleic acid insert or its complement, wherein the first and second extension products are capable of annealing to each other at both of their terminal ends, and wherein the nucleic acids of the first and second extension products together comprise a sequence for replication in a host and the desired nucleic acid insert;

optionally repeating the generating first and second extension products; and combining and annealing the first and second extension products to form a partially double-stranded, replication-competent vector.

2. A method as claimed in claim 1, further comprising transforming the partially double-stranded, replication-competent vector into an appropriate host.

3. A method as claimed in claim 1, further comprising repairing the partially double-stranded vector.

4. A method as claimed in claim 1, wherein the vector in the sample having the desired nucleic insert is a pCR-Script vector or is derived from a pCR-Script vector.

5. A method as claimed in claim 1, wherein a vector in the sample having the desired nucleic acid insert has a linear nucleic acid structure.

6. A method as claimed in claim 5, wherein the vector is a lambda bacteriophage-derived vector.

7. A method as claimed in claim 6, wherein the vector is a lambda ZAP II vector or a vector derived from lambda ZAP II.

8. A method as claimed in claim 6, wherein at least one primer contains a sequence capable of annealing to an f1 sequence of the vector during an extension reaction.

9. A method as claimed in claim 1, further comprising adding modified nucleotides capable of being incorporated into an extension product.

10. A method as claimed in claim 9, further comprising adding a reagent substantially incapable of cleaving nucleic acids with one or more incorporated modified nucleotides and capable of cleaving other unmodified nucleic acids.

11. A method as claimed in claim 1, wherein the nucleic acids of the first and second extension products together comprise a region encoding a selectable marker.

12. A method as claimed in claim 1, wherein the step of generating the first and second extension products employs an amplification reaction.

13. A method for producing a vector comprising a desired nucleic acid insert from a sample comprising a plurality of vectors, the method comprising:

generating first and second extension products from first and second primers annealed to a vector in the sample, wherein the vector comprises a desired nucleic acid insert, wherein the first and second primers anneal to complementary strands of a vector comprising the desired nucleic acid insert, wherein one or both of the first or second primers contain a nucleic acid sequence found in the desired nucleic acid insert or its complement;

providing a nucleic acid comprising an additional vector sequence, wherein the nucleic acids of the first and second extension products together with the additional vector sequence comprise a sequence for replication in a host and comprise the desired nucleic acid insert, and wherein the first and second extension products are capable of annealing to the additional vector sequence;

optionally repeating the step of generating first and second extension products; and combining and annealing the first and second extension products and the nucleic acid comprising an additional vector sequence to form a partially double-stranded, replication-competent vector.

14. A method as claimed in claim 13, further comprising transforming the partially double-stranded, replication-competent vector into an appropriate host.

15. A method as claimed in claim 13, further comprising repairing the partially double-stranded vector.

16. A method as claimed in claim 13, wherein the vector in the sample having the desired nucleic insert is a pCR-Script vector of a vector derived from a pCR-Script vector.

17. A method as claimed in claim 13, wherein a vector in the sample having the desired nucleic acid insert has a linear nucleic acid structure.

18. A method as claimed in claim 17, wherein the vector is a lambda bacteriophage-derived vector.

19. A method as claimed in claim 18, wherein the vector is a lambda ZAP II vector or a vector derived from a lambda ZAP II vector.

20. A method as claimed in claim 13, further comprising adding modified nucleotides capable of being incorporated into an extension product.

21. A method as claimed in claim 20, further comprising adding a reagent substantially incapable of cleaving nucleic acids with one or more incorporated modified nucleotides and capable of cleaving other unmodified nucleic acids.

22. A method as claimed in claim 13, wherein the nucleic acids of the first and second extension products together with the nucleic acid having an additional vector sequence comprise a region encoding a selectable marker.

23. A method as claimed in claim 13, wherein each of the first and second extension products have regions of nucleic acids at both the 3' and 5' termini that are complementary to regions of the nucleic acid having an additional vector sequence.

24. A method as claimed in claim 13, wherein the step of generating the first and second extension products employs an amplification reaction.

25. A method for producing a vector from a sample comprising a library of nucleic acid sequences, comprising:

denaturing the nucleic acids in the sample;

performing one or more amplification reactions by adding amplification reagents and primers such that a first primer pair is capable of initiating the amplification of a first extension product made with a nucleic acid comprising a vector, and a second primer pair is capable of initiating the amplification of a second extension product made with the nucleic acid comprising the vector, whereby the first and second extension products together comprise a sequence for replication in a host and a desired nucleic acid insert, and wherein the first and second extension products comprise nucleic acid regions capable of allowing the first and second extension products to anneal to each other at both their terminal ends; and annealing the first and second extension products to form a replication-competent vector.

26. A method as claimed in claim 25, further comprising transforming the replication-competent vector into an appropriate host.

27. A method as claimed in claim 25, wherein the library comprises DNA inserts linked to a pCR-Script vector or a vector derived from a pCR-Script vector.

28. A method as claimed in claim 25, wherein the library comprises a vector having a linear nucleic acid structure.

29. A method as claimed in claim 28, wherein the vector of the library is a lambda bacteriophage-derived vector.

30. A method as claimed in claim 29, wherein the vector of the library is a lambda ZAP II vector or a vector derived from a lambda ZAP II vector.

31. A method as claimed in claim 25, further comprising adding modified nucleotides capable of being incorporated into an extension product.

32. A method as claimed in claim 25, further comprising adding a reagent substantially incapable of cleaving nucleic acids with one or more incorporated modified nucleotides and capable of cleaving other nucleic acids.

33. A method as claimed in claim 25, wherein the nucleic acids of the first and second extension products together comprise a region encoding a selectable marker.

34. A method as claimed in claim 25, wherein each of the first and second extension products have regions of complementary nucleic acids at the 3' and 5' termini.

35. A method as claimed in claim 25, wherein the primers contain regions of non-priming sequence capable of allowing sequence-independent ligation between the first and second extension products.

36. A method as claimed in claim 25, wherein one or more primers comprise a sequence of nucleotides capable of introducing a site-specific, insertion, or deletion mutation into the first or second extension product.

37. A method as claimed in one of claim 1, 13, or 25 wherein the primers contain regions of non-priming sequence capable of allowing sequence-independent ligation between the extension products and additional vector sequence.

38. A method for enriching the amount of a desired nucleic acid in a sample comprising a mixture of nucleic acids comprising:

producing a vector comprising the desired nucleic acid;

generating first and second extension products from first and second primers annealed to the vector in the sample, wherein the vector comprises the desired nucleic acid, wherein the first and second primers anneal to complementary strands of a vector comprising the desired nucleic acid insert, wherein one or both of the first or second primers comprise a nucleic acid sequence found in the desired nucleic acid insert or its complement, wherein the first and second extension products are capable of annealing to each other at both of their terminal ends, and wherein the nucleic acids of the first and second extension products together comprise a sequence for replication in a host and the desired nucleic acid insert;

optionally repeating the generating first and second extension products; and combining and annealing the first and second extension products to form a partially double-stranded, replication-competent vector.

39. A method for enriching the amount of a desired nucleic acid in a sample comprising a mixture of nucleic acids, comprising:

producing a vector comprising the desired nucleic acid;

generating first and second extension products from first and second primers annealed to a vector in the sample, wherein the vector comprises a desired nucleic acid inser, wherein the first and second primers anneal to complementary strands of the vector comprising a desired nucleic acid insert, wherein one or both of the first or second primers contain a nucleic acid sequence found in the desired nucleic acid insert or its complement;

providing a nucleic acid comprising an additional vector sequence, wherein the nucleic acids of the first and second extension products together with the additional vector sequence comprise a sequence for replication in a host and comprise the desired nucleic acid insert, and wherein the first and second extension products are capable of annealing to the additional vector sequence;

optionally repeating the step of generating first and second extension products; and combining and annealing the first and second extension products and the nucleic acid comprising an additional vector sequence to form a partially stranded—stranded, replication-competent vector.

40. A method for enriching the amount of a desired nucleic acid in a sample comprising a library of nucleic acid sequences, comprising:

denaturing the nucleic acids in the sample;

performing one or more amplification reactions by adding amplification reagents and primers such that a first primer pair is capable of initiating the amplification of a first extension product made with a vector comprising a desired nucleic acid, and a second primer pair is capable of initiating the amplification of a second extension product made with the vector comprising the desired nucleic acid, whereby the first and second extension products together comprise a sequence for replication in a host and a desired nucleic acid, and wherein the first and second extension products comprise nucleic acid regions capable of allowing the first and second extension products to anneal to each other; and annealing the first and second extension products to form a replication-competent vector.

* * * * *

```
                            SEQUENCE LISTING

<160> NUMBER OF SEQ ID NOS: 26

<210> SEQ ID NO 1
<211> LENGTH: 34
<212> TYPE: DNA
<213> ORGANISM: Unknown
<220> FEATURE:
<223> OTHER INFORMATION: Description of Unknown Organism:bacterial
      plasmid chloramphenicol resistance gene

<400> SEQUENCE: 1
cacattcttg cccgcctgat gaatgctcat ccgg                              34

<210> SEQ ID NO 2
<211> LENGTH: 34
<212> TYPE: DNA
<213> ORGANISM: Unknown
<220> FEATURE:
<223> OTHER INFORMATION: Description of Unknown Organism:bacterial
      plasmid chloramphenicol resistance gene

<400> SEQUENCE: 2
ccggatgagc attcatcagg cgggcaagaa tgtg                              34

<210> SEQ ID NO 3
<211> LENGTH: 34
<212> TYPE: DNA
<213> ORGANISM: Bacteriophage f1

<400> SEQUENCE: 3
cgtggactcc aacgtcaaag ggcgaaaaac cgtc                              34

<210> SEQ ID NO 4
<211> LENGTH: 34
<212> TYPE: DNA
<213> ORGANISM: Bacteriophage f1

<400> SEQUENCE: 4
gacggttttt cgcccttttga cgttggagtc cacg                             34
```

```
<210> SEQ ID NO 5
<211> LENGTH: 31
<212> TYPE: DNA
<213> ORGANISM: Homo sapiens

<400> SEQUENCE: 5
ctacgggccg cttctcgggc tccgtcagtg g                              31

<210> SEQ ID NO 6
<211> LENGTH: 31
<212> TYPE: DNA
<213> ORGANISM: Rattus rattus

<400> SEQUENCE: 6
ctacgagacc cttctcgggc tctgtcagtg g                              31

<210> SEQ ID NO 7
<211> LENGTH: 24
<212> TYPE: DNA
<213> ORGANISM: Homo sapiens

<400> SEQUENCE: 7
gtgcaacaaa gggacccttt ctat                                      24

<210> SEQ ID NO 8
<211> LENGTH: 24
<212> TYPE: DNA
<213> ORGANISM: Rattus rattus

<400> SEQUENCE: 8
gtgcaacaaa ggagcccttt ctag                                      24

<210> SEQ ID NO 9
<211> LENGTH: 31
<212> TYPE: DNA
<213> ORGANISM: Homo sapiens

<400> SEQUENCE: 9
ccactgacgg agcccgagaa gcggcccgta g                              31

<210> SEQ ID NO 10
<211> LENGTH: 31
<212> TYPE: DNA
<213> ORGANISM: Rattus rattus

<400> SEQUENCE: 10
ccactgacag agcccgagaa gggtctcgta g                              31

<210> SEQ ID NO 11
<211> LENGTH: 21
<212> TYPE: DNA
<213> ORGANISM: Homo sapiens

<400> SEQUENCE: 11
gccgccttct cgaaagatga g                                         21

<210> SEQ ID NO 12
<211> LENGTH: 21
<212> TYPE: DNA
<213> ORGANISM: Rattus rattus

<400> SEQUENCE: 12
gctgtcttct cgaaagatga g                                         21
```

<210> SEQ ID NO 13
<211> LENGTH: 31
<212> TYPE: DNA
<213> ORGANISM: Homo sapiens

<400> SEQUENCE: 13
ctacgggccg cttctcgggc tccgtcagtg g    31

<210> SEQ ID NO 14
<211> LENGTH: 24
<212> TYPE: DNA
<213> ORGANISM: Homo sapiens

<400> SEQUENCE: 14
gtgcaacaaa gggacccttt ctat    24

<210> SEQ ID NO 15
<211> LENGTH: 31
<212> TYPE: DNA
<213> ORGANISM: Homo sapiens

<400> SEQUENCE: 15
ccactgacgg agcccgagaa gcggcccgta g    31

<210> SEQ ID NO 16
<211> LENGTH: 21
<212> TYPE: DNA
<213> ORGANISM: Homo sapiens

<400> SEQUENCE: 16
gccgccttct cgaaagatga g    21

<210> SEQ ID NO 17
<211> LENGTH: 34
<212> TYPE: DNA
<213> ORGANISM: Bacteriophage f1

<400> SEQUENCE: 17
gccatcgccc tgatagacgg ttttcgccc tttg    34

<210> SEQ ID NO 18
<211> LENGTH: 32
<212> TYPE: DNA
<213> ORGANISM: Homo sapiens

<400> SEQUENCE: 18
ctcatgaaga tcctcaccga gcgcggctac ag    32

<210> SEQ ID NO 19
<211> LENGTH: 34
<212> TYPE: DNA
<213> ORGANISM: Bacteriophage f1

<400> SEQUENCE: 19
ccagtttgga acaagagtcc actattaaag aacg    34

<210> SEQ ID NO 20
<211> LENGTH: 31
<212> TYPE: DNA
<213> ORGANISM: Homo sapiens

<400> SEQUENCE: 20

```
gccggactcg tcatactcct gcttgctgat c                              31

<210> SEQ ID NO 21
<211> LENGTH: 31
<212> TYPE: DNA
<213> ORGANISM: Homo sapiens

<400> SEQUENCE: 21
atggatgatg atatcgccgc gctcgtcgtc g                              31

<210> SEQ ID NO 22
<211> LENGTH: 32
<212> TYPE: DNA
<213> ORGANISM: Homo sapiens

<400> SEQUENCE: 22
ctgtagccgc gctcggtgag gatcttcatg ag                             32

<210> SEQ ID NO 23
<211> LENGTH: 30
<212> TYPE: DNA
<213> ORGANISM: Unknown
<220> FEATURE:
<223> OTHER INFORMATION: Description of Unknown Organism:bacterial
      plasmid ampicillin resistance gene

<400> SEQUENCE: 23
cactaaaggg gtgcgcggaa ccccctatttg                               30

<210> SEQ ID NO 24
<211> LENGTH: 30
<212> TYPE: DNA
<213> ORGANISM: Unknown
<220> FEATURE:
<223> OTHER INFORMATION: Description of Unknown Organism:bacterial
      plasmid ampicillin resistance gene

<400> SEQUENCE: 24
gcgtaatacg gagtaaactt ggtctgacag                                30

<210> SEQ ID NO 25
<211> LENGTH: 30
<212> TYPE: DNA
<213> ORGANISM: ampicillin resistance gene

<400> SEQUENCE: 25
ttccgcgcac ccctttagtg agggttaatt                                30

<210> SEQ ID NO 26
<211> LENGTH: 30
<212> TYPE: DNA
<213> ORGANISM: ampicillin resistance gene

<400> SEQUENCE: 26
aagtttactc cgtattacgc gcgctcactg                                30
```